United States Patent
Geimer et al.

(10) Patent No.: US 9,764,002 B2
(45) Date of Patent: Sep. 19, 2017

(54) DOSAGE REGIMEN FOR THERAPEUTIC METHOD

(71) Applicant: MADELEINE PHARMACEUTICALS PTY LTD, Mount Barker (AU)

(72) Inventors: Thomas Robert Geimer, Emu Bay (AU); Richard Neil Upton, Adelaide (AU)

(73) Assignee: MADELEINE PHARMACEUTICALS PTY LTD (AU)

( * ) Notice: Subject to any disclaimer, the term of this patent is extended or adjusted under 35 U.S.C. 154(b) by 0 days.

(21) Appl. No.: 14/853,799

(22) Filed: Sep. 14, 2015

(65) Prior Publication Data

US 2016/0051631 A1 Feb. 25, 2016

Related U.S. Application Data

(63) Continuation-in-part of application No. PCT/AU2014/000256, filed on Mar. 14, 2014.

(60) Provisional application No. 61/789,557, filed on Mar. 15, 2013.

(51) Int. Cl.
| | | |
|---|---|---|
| *A61K 38/22* | (2006.01) | |
| *A61K 38/00* | (2006.01) | |
| *A61K 38/16* | (2006.01) | |
| *A61K 9/00* | (2006.01) | |
| *A61M 5/168* | (2006.01) | |
| *A61M 5/142* | (2006.01) | |

(52) U.S. Cl.
CPC ........ *A61K 38/2242* (2013.01); *A61K 9/0019* (2013.01); *A61K 38/16* (2013.01); *A61M 5/16804* (2013.01); *A61M 2005/14208* (2013.01)

(58) Field of Classification Search
None
See application file for complete search history.

(56) References Cited

U.S. PATENT DOCUMENTS

| | | | |
|---|---|---|---|
| 5,691,310 A | 11/1997 | Vesely | |
| 2005/0113286 A1 | 5/2005 | Schrreiner et al. | |
| 2007/0141634 A1 | 6/2007 | Vuolteenaho et al. | |
| 2009/0062730 A1 | 3/2009 | Woo | |
| 2012/0277155 A1* | 11/2012 | VanAntwerp | A61K 9/0019 514/12.4 |
| 2017/0020899 A1 | 1/2017 | Geimer | |

FOREIGN PATENT DOCUMENTS

| | | |
|---|---|---|
| WO | WO 2009/040031 | 4/2009 |
| WO | WO 2012-019237 A1 | 2/2012 |
| WO | WO 2012/115771 | 8/2012 |
| WO | WO 2012/115772 | 8/2012 |
| WO | WO 2013/154784 | 10/2013 |
| WO | WO 2014/138796 | 9/2014 |

OTHER PUBLICATIONS

GenBank accession XP_001141705.1 (Oct. 25, 2012).
Saito et al., "Clinical application of atrial natriuretic polypeptide in patients with congestive heart failure: beneficial effects on left ventricular function"; Circulation, vol. 76, No. 1, pp. 115-124 (Jul. 1987).
Vesely et al., "Vessel dilator enchances sodium and water excretion and has beneficial hemodynamic effects in persons with congestive heart failure"; Circulation, vol. 98, No. 4, pp. 323-329 (Jul. 1998).
International Search Report prepared by the Korean Intellectual Property Office on Jun. 11, 2014 for International Application No. PCT/AU2014/000256.
Lenz et al. "Cardiac hormones eliminate some human squamous lung carcinomas in athymic mice," European Journal of Clinical Investigation, Mar. 2010, vol. 40, No. 3, pp. 242-249.
Vesely "Which of the Cardiac Natriuretic Peptides is Most Effective for the Treatment of Congestive Heart Failure, Renal Failure and Cancer?" Clinical and Experimental Pharmacology and Physiology, Mar. 2006, vol. 33, No. 3, pp. 169-176.
Extended Search Report for European Patent Application No. 14763641.9, dated Jul. 25, 2016, 12 pages.
Bonios et al. "The challenge of treating congestion in advanced heart failure, "Expert Reviews of Cardiovascular Therapy, 2011, vol. 9, No. 9, pp. 1181-1191.
Patel et al. "Combined Treatment with Vessel Dilator and Kaliuretic Hormone in Persons with Congestive Heart Failure," Experimental Biology and Medicine, 2004, vol. 229, pp. 521-527.
Teerlink et al. "Serelaxin, recombinant human relaxin-2, for treatment of acute heart failure (RELAX-AHF): a randomised, placebo-controlled trial," Lancet, Jan. 2013, vol. 381, pp. 29-39.
Vardeny et al. "First-in-Class Angiotensin Receptor Neprilysin Inhibitor in Heart Failure," Clinical Pharmacology & Therapeutics, Oct. 2013, vol. 94, No. 4, pp. 445-448.

(Continued)

*Primary Examiner* — Shulamith H Shafer
(74) *Attorney, Agent, or Firm* — Sheridan Ross P.C.

(57) ABSTRACT

Disclosed herein is the use of an active agent comprising a peptide derived from atrial natriuretic peptide (ANP) prohormone or a mimetic thereof in the manufacture of a medicament for treating a disease in a subject. The medicament is administered subcutaneously in a multimodal dosage regime comprising at least an initial dosage stage and at least one maintenance dosage stage. The initial dosage stage comprises infusing the active agent at an initial dosage rate for an initial period to achieve a target steady state blood plasma concentration of the active agent or metabolite thereof. The maintenance dosage stage(s) comprise(s) adjusting the dosage rate to a maintenance dosage rate for a maintenance period to substantially maintain said target steady state blood plasma concentration of the active agent or metabolite thereof.

17 Claims, 18 Drawing Sheets

(56) References Cited

OTHER PUBLICATIONS

Vesely et al. "Three Peptides From the Atrial Natriuretic Factor Prohormone Amino Terminus Lower Blood Pressure and Produce Diuresis, Natriuresis, and/or Kaliuresis in Humans," Circulation, Sep. 1994, vol. 90, No. 3, pp. 1129-1140.

Vesely et al. "Comparison of vessel dilator and long-acting natriuretic peptide in the treatment of congestive heart failure," American Heart Journal, Oct. 1999, vol. 138, No. 4, Part 1, pp. 625-632.

* cited by examiner

SEQUENCE LISTING

<160> NUMBER OF SEQ ID NOS: 4

<210> SEQ ID NO 1
<211> LENGTH: 37
<212> TYPE: PRT
<213> ORGANISM: Homo sapiens

<400> SEQUENCE: 1

```
Glu Val Val Pro Pro Gln Val Leu Ser Glu Pro Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35
```

<210> SEQ ID NO 2
<211> LENGTH: 37
<212> TYPE: PRT
<213> ORGANISM: Pongo pygmaeus

<400> SEQUENCE: 2

```
Glu Val Val Pro Pro Gln Val Leu Ser Glu Gln Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35
```

<210> SEQ ID NO 3
<211> LENGTH: 37
<212> TYPE: PRT
<213> ORGANISM: Macaca mulatta

<400> SEQUENCE: 3

```
Glu Val Val Pro Pro Gln Val Leu Arg Glu Gln Asn Glu Glu Ala Gly
1               5                   10                  15

Ala Ala Leu Ser Pro Leu Pro Glu Val Pro Pro Trp Thr Gly Asp Val
            20                  25                  30

Ser Pro Ala Gln Arg
        35
```

<210> SEQ ID NO 4
<211> LENGTH: 37
<212> TYPE: PRT
<213> ORGANISM: Felis catus

<400> SEQUENCE: 4

```
Glu Val Val Pro Pro Gln Val Leu Ser Glu Gln Asn Glu Glu Ala Gly
1               5                   10                  15

Ala Ala Leu Ser Pro Leu Pro Glu Val Pro Pro Trp Ala Gly Glu Val
            20                  25                  30

Asn Pro Ala Gln Arg
        35
```

DOSAGE REGIMEN FOR THERAPEUTIC METHOD

CROSS-REFERENCE TO RELATED APPLICATIONS

The application is a continuation-in-part of International Application No. PCT/AU2014/000256 filed Mar. 14, 2014, which claims priority from U.S. Provisional Patent Application No. 61/789,557 titled "DOSAGE REGIMEN FOR THERAPEUTIC METHOD" and filed on 15 Mar. 2013, the contents of which are hereby incorporated by reference in their entirety.

REFERENCE TO SEQUENCE LISTING

This application contains a Sequence Listing submitted as an electronic text file named "Sequence_Listing_ST25_1134891_1.TXT", having a size in bytes of 2 kb, and created on Sep. 14, 2015. The information contained in this electronic file is hereby incorporated by reference in its entirety pursuant to 37 CFR §1.52(e)(5).

TECHNICAL FIELD

The present invention relates to methods and apparatus for treating subjects with peptides derived from atrial natriuretic peptide (ANP) prohormone or mimetics thereof.

BACKGROUND

Atrial natriuretic peptide (ANP) is a protein secreted by heart muscle cells which regulates blood pressure and maintains plasma volume in healthy individuals by mediating natriuretic, diuretic and haemodynamic effects. Vessel dilator (VSDL) is a naturally occurring 37 amino acid cardiac peptide consisting of amino acids 31-67 of the 126 amino acid ANP. The main biological activity of VSDL is to regulate blood pressure and maintain plasma volume in healthy individuals by mediating natriuretic, diuretic and haemodynamic effects (Vesely, 2003).

Investigations into the use of VSDL for the treatment of cardiac diseases such as congestive heart failure (CHF) have been conducted via both preclinical and human clinical studies. It has been shown that VSDL can significantly improve haemodynamic and renal parameters, such as cardiac index/output, pulmonary capillary wedge pressure, systemic and pulmonary vascular resistance, natriuresis, diuresis, and creatinine clearance without any symptomatic side effects (Vesely, 1994 and 1998). VSDL is considered to be a safe and potential effective treatment by mediating beneficial haemodynamic effects including, but not limited to, beneficial natriuretic, diuretic and renal effects, through mechanisms of regulating plasma volume and blood pressure (BP) within clinically acceptable ranges and without seriously adverse side effects. Accordingly, VSDL can be administered to subjects with acute decompensated congestive heart failure (ADCHF). Moreover, VSDL has also been found to have anticancer effects (Skelton et al. 2011), and is a promising candidate in the treatment of acute renal failure (Vesely, 2003). Accordingly, it will be appreciated that VSDL is a useful candidate for the treatment of various diseases.

The present applicant has surprisingly found that when a human subject is dosed with VSDL a steady state blood plasma concentration (Css) of the active agent is not necessarily achieved in accordance with classical pharmacokinetic dosage calculations.

SUMMARY

The present invention arises from clinical studies during which VSDL was infused subcutaneously into subjects at a dosage rate that was predicted, based on previous clinical data and standard pharmacokinetic calculations, to provide a steady state blood plasma concentration of VSDL within 6 hours. However, what was clinically observed was that the blood plasma concentration did not reach the calculated steady state concentration but rather, continued to increase beyond the steady state concentration that was calculated would be achieved based upon the dosage rate administered. As a result of these clinical studies, the present applicant has developed a novel dosage regime for administration of VSDL and related atrial natriuretic peptide (ANP) prohormone peptides. The dosage regime takes into account the non-classical pharmacokinetic behaviour of VSDL.

Accordingly, in a first aspect the present invention provides the use of an active agent comprising a peptide derived from atrial natriuretic peptide (ANP) prohormone or a mimetic thereof in the manufacture of a medicament for treating a disease in a subject, wherein said medicament is administered subcutaneously in a multimodal dosage regime comprising at least an initial dosage stage and at least one maintenance dosage stage, the initial dosage stage comprising infusing the active agent at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof.

In a second aspect, the present invention provides an apparatus for administering an active agent comprising a peptide derived from atrial natriuretic peptide (ANP) prohormone or a mimetic thereof to a subject in need of treatment of a disease, the apparatus comprising: (i) an infusion device for delivery of the active agent to the subject subcutaneously; and (ii) a control unit operated by a series of commands, wherein the series of commands contains a set of instructions that causes the device to administer the active agent to the subject in a multimodal dosage regime comprising at least an initial dosage stage and at least one maintenance dosage stage, the initial dosage stage comprising infusing the active ingredient at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof.

In embodiments of the second aspect of the invention the apparatus further comprises (iii) a monitoring unit capable of adjusting the control unit to achieve the target steady state blood plasma concentration.

In a third aspect, the present invention provides a peptide derived from atrial natriuretic peptide (ANP) prohormone or a mimetic thereof for use in the treatment of a disease in a subject, wherein said peptide or mimetic thereof is administered subcutaneously in a multimodal dosage regime comprising at least an initial dosage stage and at least one maintenance dosage stage, the initial dosage stage comprising infusing the peptide or mimetic thereof at an initial dosage rate for an initial period to achieve a target steady state blood plasma concentration of the peptide or mimetic thereof or metabolite thereof, and the maintenance dosage stage(s) comprising adjusting the dosage rate to a maintenance dosage rate for a maintenance period to substantially maintain said target steady state blood plasma concentration of the peptide or mimetic thereof or metabolite thereof.

In embodiments of the first, second and third aspects the disease is selected from the group consisting of cardio-renal syndromes and cancer. Cardio-renal syndromes to be treated include, but are not limited to, chronic congestive heart failure (CHF), acute decompensated congestive heart failure (ADCHF), pulmonary arterial hypertension (PAH), acute renal failure, chronic renal failure, and acute kidney injury (AKI).

In a fourth aspect, the present invention provides a method of treating a cardio-renal syndrome or cancer in a subject, said method comprising administering subcutaneously to the subject an effective amount of an active agent comprising a peptide derived from atrial natriuretic peptide (ANP) prohormone or a mimetic thereof in a multimodal dosage regime comprising at least an initial dosage stage and at least one maintenance dosage stage, the initial dosage stage comprising infusing the active agent at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof.

In embodiments of the first to fourth aspects, the multimodal dosage regime is a bimodal regime comprising the initial dosage stage and a maintenance dosage stage.

In a fifth aspect, the present invention provides a diagnostic test comprising obtaining a test sample of blood from a subject, determining the blood plasma concentration of the peptide derived from atrial natriuretic peptide (ANP) prohormone or a mimetic thereof, and providing information on the blood plasma concentration.

In embodiments of the fifth aspect, the method further comprises using the results of the blood plasma concentration to adjust the dosage rate during administration of the peptide derived from atrial natriuretic peptide (ANP) prohormone or a mimetic thereof to the subject.

In a sixth aspect, the present invention provides a method of monitoring the blood plasma levels of a peptide derived from atrial natriuretic peptide (ANP) prohormone or a mimetic thereof in order to optimise dosing or scheduling, the method comprising:
  (i) contacting a test blood sample obtained from a subject with a first capture binding agent that binds to the peptide derived from atrial natriuretic peptide (ANP) prohormone or a mimetic or fragment thereof to form a first capture binding agent-peptide complex;
  (ii) contacting the first capture binding agent-peptide complex with a second detection binding agent that binds to the peptide derived from atrial natriuretic peptide (ANP) prohormone or a mimetic or fragment thereof and is conjugated to a detectable label to form a detection-capture binding agent-peptide complex;
  (iii) determining the amount of the detection-capture binding agent-peptide complex formed by detecting the detectable label, wherein the amount of the detection-capture binding agent-peptide complex formed is the amount of the peptide derived from atrial natriuretic peptide (ANP) prohormone or a mimetic thereof contained in the test sample; and
  (iv) comparing the amount of the peptide derived from atrial natriuretic peptide (ANP) prohormone or a mimetic thereof in the test sample determined in step (iii) with a desired blood plasma level.

In a seventh aspect, the present invention provides a method of optimising dosing of an active agent comprising a peptide derived from atrial natriuretic peptide (ANP) prohormone or a mimetic thereof to a subject, the method comprising:
  (i) administering subcutaneously to the subject an effective amount of the active agent in a multimodal dosage regime comprising at least an initial dosage stage and at least one maintenance dosage stage, the initial dosage stage comprising infusing the active agent at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof;
  (ii) determining the concentration of at least one renal function biomarker in a body fluid of the subject at two or more time points;
  (iii) comparing the concentrations of the at least one renal function biomarker at the two or more time points to ascertain whether renal function of the subject has improved over time;
  (iv) using the data obtained from step (iii) to determine whether the dosage rate of the active agent should be adjusted; and
  (v) if necessary, adjusting the dosage rate of the active agent during the initial dosage stage and/or the maintenance dosage stage(s) based on the determination made at step (iv).

In embodiments of the seventh aspect, the renal function biomarker is creatinine. In these embodiments, an increase in the concentration of creatinine in the body fluid of the subject over time indicates impairment of renal function whereas a decrease in the concentration of creatinine in the body fluid of the subject over time indicates an improvement of renal function. In embodiments, the rate of change in the concentration of creatinine in the body fluid of the subject over time can be used to adjust the dosage rate of the active agent.

DETAILED DESCRIPTION

Figure 1:
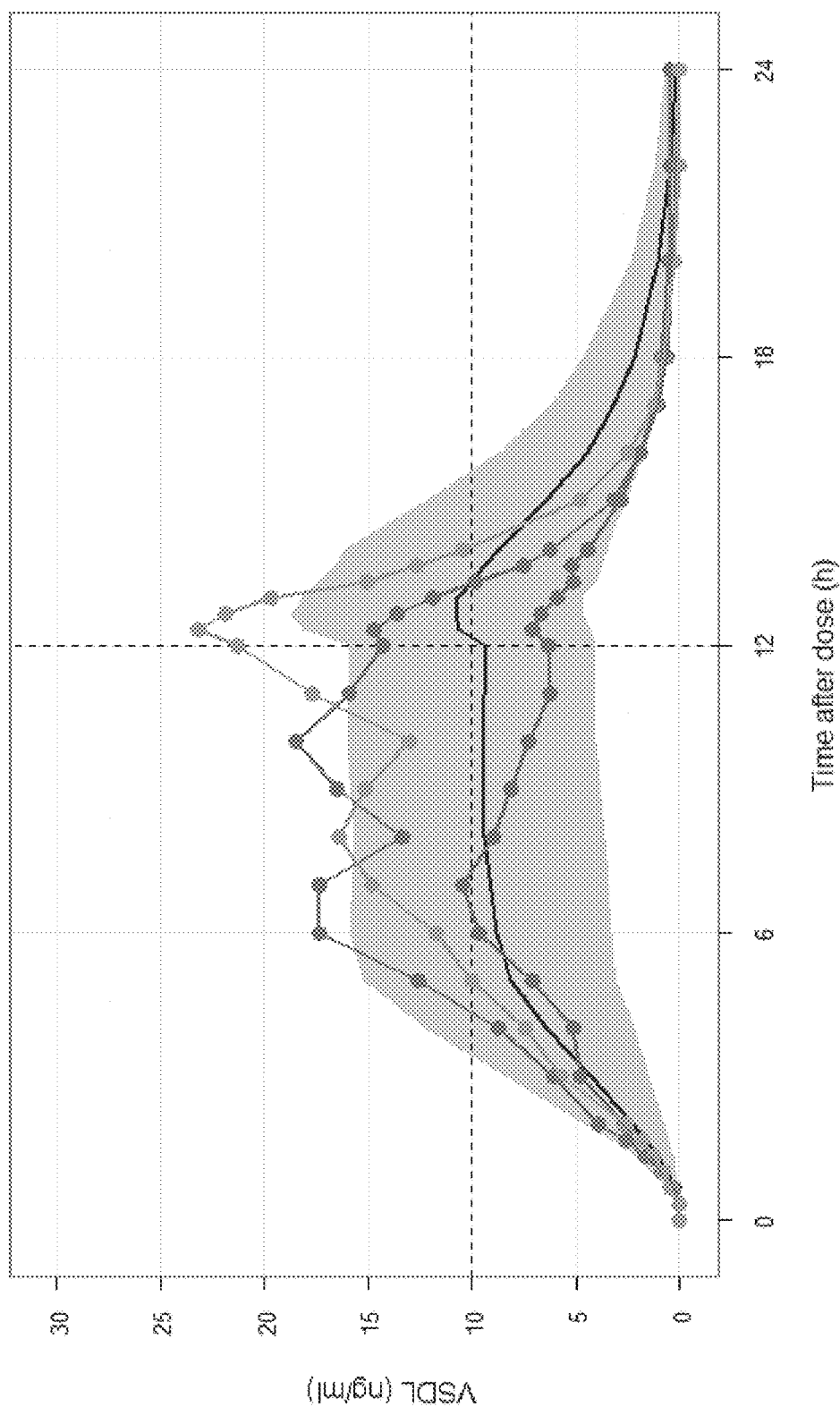
FIG. 1 shows a plot of time (h) after dose vs blood plasma VSDL concentration (ng/ml) for three subjects. The black line and ribbon is the mean and 90% CI predicted for 1000 patients and the symbols are the observed data.

In a first aspect, the present invention provides the use of an active agent comprising a peptide derived from atrial natriuretic peptide (ANP) prohormone or a mimetic thereof in the manufacture of a medicament for treating a disease in a subject, wherein said medicament is administered subcutaneously in a multimodal dosage regime comprising at least an initial dosage stage and at least one maintenance dosage stage, the initial dosage stage comprising infusing the active agent at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof.

The multimodal dosage regime is not for a fixed time nor based on classical pharmacokinetic dosage calculations but rather the result of sophisticated modelling of hypothetical and observed behaviour of VSDL, or other peptides from the ANP prohormone in the human body.

A "steady state concentration" in a human subject receiving treatment is a concentration of the peptide derived from atrial natriuretic peptide (ANP) prohormone or a mimetic or metabolite thereof that is at a dynamic equilibrium, fluctuating periodically within a reasonably predictable and periodic range with the fluctuation determined by the dosing schedule.

In embodiments, the target steady state blood plasma concentration is greater than 10 ng/ml. In some embodiments, the target steady state blood plasma concentration is greater than 15 ng/ml. In some embodiments, the target steady state blood plasma concentration is from about 15 ng/ml to about 25 ng/ml. In embodiments, the target steady state blood plasma concentration is 15 ng/ml, 16 ng/ml, 17 ng/ml, 18 ng/ml, 19 ng/ml, 20 ng/ml, 21 ng/ml, 22 ng/ml, 23 ng/ml, 24 ng/ml or 25 ng/ml.

In some other embodiments, the dosage regime is a "low dose" regime and the target steady state blood plasma concentration is from about 1 ng/ml to about 15 ng/ml or from about 3 ng/ml to about 15 ng/ml. In some specific embodiments of the low dose regime, the target steady state blood plasma concentration is from about 5 ng/ml to about 10 ng/ml. In embodiments, the target "low dose" steady state blood plasma concentration is 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml or 14 ng/ml. In specific embodiments, the target "low dose" steady state blood plasma concentration is about 5 ng/ml. In other specific embodiments, the target "low dose" steady state blood plasma concentration is about 10 ng/ml. In still other specific embodiments, the target "low dose" steady state blood plasma concentration is about 15 ng/ml.

As used herein, the term "about" when used in reference to a steady state blood plasma concentration means the steady state blood plasma concentration is within ±10% of the stated value.

The gene encoding for the synthesis of the atrial natriuretic peptide (ANP) prohormone consists of three exons and two introns. Exon 1 encodes the signal peptide and the first 16 amino acids of the ANP prohormone. These 16 amino acids form the N-terminus of a peptide hormone named long-acting natriuretic hormone (LANH). Exon 2 of the proANP gene encodes for three peptide hormones, namely vessel dilator, kaliuretic hormone, and ANP. Therefore, as used herein, the term "peptide derived from atrial natriuretic peptide (ANP) prohormone or a mimetic thereof" includes within its scope long-acting natriuretic hormone (LANH), vessel dilator (VSDL), kaliuretic hormone (KP), and ANP.

In specific embodiments, the peptide derived from atrial natriuretic peptide (ANP) prohormone or a mimetic thereof is vessel dilator (VSDL). VSDL is a naturally occurring 37 amino acid (aa) peptide, which is produced in vivo following processing of the 126 amino acid atrial natriuretic peptide (ANP, also known as atrial natriuretic factor (ANF)) pro-hormone (proANP; Vesely, 2003). VSDL consists of amino acids 31-67 of the ANP prohormone. The VSDL for use herein may comprise the native amino acid sequence of human VSDL, namely (SEQ ID NO: 1)
Glu-Val-Val-Pro-Pro-Gln-Val-Leu-Ser-Glu-Pro-Asn- Glu-Glu-Ala-Gly-Ala-Ala-Leu-Ser-Pro-Leu-Pro-Glu- Val-Pro-Pro-Trp-Thr-Gly-Glu-Val-Ser-Pro-Ala-Gln- Arg.

Other suitable native VSDL peptides include:

Pongo pygmaeus (common orang-utan)
(SEQ ID NO: 2)
Glu-Val-Val-Pro-Pro-Gln-Val-Leu-Ser-Glu-Gln-Asn- Glu-Glu-Ala-Gly-Ala-Ala-Leu-Ser-Pro-Leu-Pro-Glu- Val-Pro-Pro-Trp-Thr-Gly-Glu-Val-Ser-Pro-Ala-Gln- Arg;

Macaca mulatta (rhesus monkey)
(SEQ ID NO: 3)
Glu-Val-Val-Pro-Pro-Gln-Val-Leu-Arg-Glu-Gln-Asn- Glu-Glu-Ala-Gly-Ala-Ala-Leu-Ser-Pro-Leu-Pro-Glu- Val-Pro-Pro-Trp-Thr-Gly-Asp-Val-Ser-Pro-Ala-Gln- Arg;
and Felis catus
(SEQ ID NO: 4)
Glu-Val-Val-Pro-Pro-Gln-Val-Leu-Ser-Glu-Gln-Asn- Glu-Glu-Ala-Gly-Ala-Ala-Leu-Ser-Pro-Leu-Pro-Glu- Val-Pro-Pro-Trp-Ala-Gly-Glu-Val-Asn-Pro-Ala-Gln- Arg.

The peptide may also be a variant of VSDL. As used herein, variants of the VSDL peptide include derivatives or mimetics of a native VSDL peptide, which include minor variations in the amino acid sequence, may be a suitable VSDL peptide for the method of the present invention providing that such derivatives, variants or mimetics of said native peptide do not result in any substantial decrease or variation in biological activity. These variations may include conservative amino acid substitutions as known to the person skilled in the art. Some specific examples of suitable amino acid substitutions within the VSDL peptide may include Pro→Gln (especially at position 41 of proANP; ie position 10 of the VSDL peptide), Thr→Ala (especially at position 59 of proANP; ie position 28 of the VSDL peptide), Glu→Asp (especially at position 61 of proANP, ie position 30 of the VSDL peptide), and Ser→Asn (especially at position 63 of proANP, ie position 32 of the VSDL peptide).

Peptides derived from ANP prohormone may be produced by any of the standard protein synthesis methods known to the person skilled in the art or by recombinant techniques involving, for example, the introduction of a polynucleotide molecule encoding the particular peptide into a suitable host cell (eg a host cell selected from bacterial cells such as *E. coli, Streptomyces* and *S. typhimurium*; fungal cells such as yeast cells; insect cells such as *Drosophila* S2 and *Spodoptera* Sf9 cells; animal cells such as Chinese hamster ovary (CHO), monkey kidney (COS) cells and human embryonic kidney 293 (HEK 293) cells; and plant cells) and culturing the cell under conditions suitable for the expression of the particular peptide.

Typically, the peptide derived from ANP prohormone or a mimetic thereof will be administered as a composition consisting of a solution or suspension of the peptide or mimetic in a pharmaceutically-acceptable carrier. However, it will be readily appreciated by the person skilled in the art, that the peptide or mimetic may be bound or associated with a carrier molecule (eg a carrier protein or fusion partner such as human serum albumin (HSA) or a polysaccharide (eg Dextran) or polyether (eg polyethylene glycol)) in order to modulate the biological activity and/or serum half-life time of the peptide or mimetic.

The pharmaceutically-acceptable carrier may be any pharmaceutically acceptable solvent, suspending agent or vehicle for delivering the peptide derived from ANP prohormone or mimetic thereof to the subject. The carrier may include one or more pharmaceutical additives of a type appropriate for subcutaneous administration, such as excipients, preservatives, stabilisers, and the like. Suitable carriers, excipients, preservatives, stabilisers and the like can be found in "Remington's Pharmaceutical Sciences" Mack Pub. Co., New Jersey (1991).

The pH of the composition may be between about pH 3 and pH 11. For example, the composition may be pH 3, pH 4, pH 5, pH 6, pH 7, pH 8, pH 9, pH 10 or pH 11.

The peptide derived from ANP prohormone or a mimetic thereof may be administered to the subject in a combination therapy.

In an earlier study, a steady state blood plasma concentration of VSDL of 10 ng/ml was achieved; it was found that the subcutaneous dose required to be infused was consistent with the known relationship $$\text{Dose} = \frac{Css \times Cl}{F}$$

where Css is the steady state concentration, Cl is the clearance and F is the bioavailability.

Steady state occurs when the amount of drug administered (in a given time period) is equal to the amount of drug eliminated in that same period. At steady state, the plasma concentration of the drug (Css) at any time during any dosing interval, as well as the peak and trough, are similar.

For the same active, doubling the dose would be expected to double the Css in the same time. However, when the dose was doubled in the clinical studies, it was found that the Css reached 20 ng/ml (ie double the earlier study), but then did not plateau but continued to increase such that it reached 30 ng/ml in some subjects.

Taking into account the non-classical pharmacokinetics of VSDL, the present applicant has developed a multimodal dosage regime comprising at least an initial dosage stage and a maintenance dosage stage. This is a bimodal dosage regime. However, it will be appreciated that the dosage regime may also comprise other dosage stages comprising administration of the active agent at a dosage rate and/or dosage period that is different to the dosage rate and/or period of the initial and maintenance dosage stages. The other dosage stages may be intermediate stages between the initial and maintenance dosage stages and/or they may follow the maintenance dosage stage.

The initial dosage rate may be, for example, in the range of from about 20 µg/hour to about 2000 µg/hour, preferably from about 40 µg/hour to about 1900 µg/hour, and more preferably from about 75 µg/hour to about 1850 µg/hour. In embodiments having a target steady state blood plasma concentration of about 10 ng/ml, the initial dosage rate may be about 900 µg/hour. In other embodiments having a target steady state blood plasma concentration of about 20 ng/ml, the initial dosage rate may be about 1800 µg/hour. In embodiments having a target steady state blood plasma concentration of about 5 ng/ml, the initial dosage rate may be, for example, in the range of about 40 µg/hour to about 450 µg/hour (eg 45 µg/hour, 55 µg/hour, 425 µg/hour or 450 µg/hour) or about 75 µg/hour to about 150 µg/hour.

In embodiments, the initial period is from about 4 to about 6 times the half-life of the active agent. In the case of VSDL, the initial period may be from about 4 hours to about 6 hours. In specific embodiments, the initial period is about 5 hours.

The maintenance dosage rate may be, for example, in the range of from about 10 µg/hour to about 1200 µg/hour, preferably from about 25 µg/hour to about 1000 µg/hour, and more preferably from about 100 µg/hour to about 750 µg/hour. In embodiments having a target steady state blood plasma concentration of about 10 ng/ml, the maintenance dosage rate may be about 550 µg/hour. In other embodiments having a target steady state blood plasma concentration of about 20 ng/ml, the maintenance dosage rate may be about 1080 µg/hour. In embodiments having a target steady state blood plasma concentration of about 5 ng/ml, the maintenance dosage rate may be, for example, in the range of about 20 µg/hour to about 270 µg/hour or about 25 µg/hour to about 150 µg/hour (eg 135 µg/hour).

In our clinical studies, lead patients were dosed at 900 µg/h for 6 hours based on the standard calculation shown earlier to reach a target steady state blood plasma concentration of 10 ng/ml and plasma levels of VSDL measured. Six hours is more than five half-lives for VSDL and, as such, should result in a steady state blood plasma concentration. Having verified the target steady state blood plasma concentration from lead patients, then Cohort 1 "Part 1" received 900 µg/h for 12 hours so as to achieve target steady state blood plasma concentration. However, the target steady state blood plasma concentration was not observed and as such the dosing regime required modification. After significant postulation and modelling of the hypothetical behaviour of VSDL, the multimodal dosage regime was developed. Cohort 1 "Part 2" was introduced using the bimodal dosing regime in an effort to reach a steady state blood plasma concentration of 10 ng/ml. Cohort 1 "Part 2" patients received VSDL at 900 µg/h (ie initial dosage rate) for 5 hours (ie initial period), followed by 550 µg/h for 7 hours (ie maintenance dosage rate).

The dosing model was then used to calculate the dosages required for a 20 ng/ml target steady state blood plasma concentration. Consequently, Cohort 2 "Part 2" received a dosing regime of 1800 µg/h for 5 hours (initial dose), followed by 1080 µg/h for 7 hours (maintenance dose) which is not simply "twice" that of the 10 ng/ml "low dose" as the model predicted the maintenance dose to be 1080 µg/hr and not 1100 µg/hr.

In one particular embodiment having a target steady state blood plasma concentration of 20 ng/ml, the initial dose is 1800 µg/h for 5 hours followed by a maintenance dose of 540 µg/h for 7 hours. In another particular embodiment having a target steady state blood plasma concentration of 5 ng/ml, the initial dose is 450 µg/h for 5 hours followed by a maintenance dose of 135 µg/h for 7 hours. Further, in another particular embodiment having a target steady state blood plasma concentration of 1 ng/ml, the initial dose is 90 µg/hour for 5 hours followed by a maintenance dose of 27 µg/hour for 7 hours.

In a second aspect, the invention provides an apparatus for administering an active agent comprising a peptide derived from atrial natriuretic peptide (ANP) prohormone or a mimetic thereof to a subject in need of treatment of a disease, the apparatus comprising: (i) an infusion device for delivery of the active agent to the subject subcutaneously; and (ii) a control unit operated by a series of commands, where the series of commands contains a set of instructions that causes the device to administer the active agent to the subject in a multimodal dosage regime comprising at least an initial dosage stage and a maintenance dosage stage, the initial dosage stage comprising infusing the active agent at an initial dosage rate for an initial period to achieve a target steady state blood plasma concentration of the active agent or metabolite thereof, and the maintenance dosage stage comprising adjusting the dosage rate to a maintenance dosage rate for a maintenance period to substantially maintain said target steady state blood plasma concentration of the active agent or metabolite thereof.

In embodiments, the infusion device comprises an infusion pump and the set of instructions provides for administering the active agent to the subject via subcutaneous infusion in a substantially continuous or continuous manner by the infusion pump.

Optionally, the infusion pump is an implantable infusion pump. An implantable infusion pump can be implanted at any suitable subcutaneous implantation site using methods and devices known in the art.

In embodiments, the set of instructions causes the infusion pump to (i) administer the active agent to the subject subcutaneously at an initial dosage rate of from about 20 µg/hour to about 2000 µg/hour for an initial period of from about 4 hours to about 6 hours, and then (ii) administer the active agent to the subject subcutaneously at a maintenance dosage rate of from about 20 µg/hour to about 1200 µg/hour.

Typically, the infusion pump will be in fluid connection with a fluid reservoir containing the active agent. The infusion pump may be provided within the reservoir or may otherwise be operably connected thereto.

The infusion pump may be a mechanical or an electromechanical pump, examples of which are described in U.S. Pat. Nos. 4,692,147; 4,360,019; 4,487,603; 4,360,019; 4,725,852; 5,820,589; 5,643,207; 6,198,966; and the like. Osmotic pumps may be particularly suitable due to their consistent controlled release and relatively small size. Suitable implantable drug infusion pumps include an Alzet® osmotic pump (Durect Corporation, Cupertino Calif., United States of America), a Duros® device (Intarcia Therapeutics, Inc., Hayward Calif., United States of America), and a Paradigm™ device (Medtronic Australasia Pty Ltd, Gladesville NSW, Australia).

The infusion device also comprises catheters, injection devices, and the like, as is known in the art. For example, the infusion device may comprise a standard catheter or implantable drug port (eg a Port-a-Cath®; Smiths Medical MD, Inc., St. Paul Minn., United States of America).

In embodiments, the control unit is not designed to accept user input. In these embodiments, the apparatus is manufactured with the control unit pre-set to administer the multimodal dosage regime. In other embodiments, the control unit is designed to allow the user to select a desired multimodal dosage regime from two or more pre-programmed multimodal dosage regimes. In other embodiments, the control unit is designed to allow the user to (i) select a desired initial dosage rate, (ii) select a desired initial period, and/or (iii) select a desired maintenance dosage rate. The desired initial dosage rate, initial period, and/or maintenance dosage rates may each be selected from a set of values programmed into the control unit.

In embodiments, the apparatus may be designed to allow the user to select a desired steady state concentration from a fixed set of values specified by the set of instructions. In these embodiments, the set of instructions can be designed to calculate and cause the device to utilise appropriate dosage amounts, dosage rates and dosage times to achieve the desired steady state concentration. For example, the apparatus may be designed to allow the user to select a steady state concentration of 10 ng/ml and the set of instructions can then calculate and cause the device to administer the active agent at an initial dosage rate of 900 µg/hour for an initial period of 5 hours and then lower the dosage rate to a maintenance dosage rate of 550 µg/hour for 7 hours. Alternatively, the apparatus may be designed to allow the user to select a steady state concentration of 20 ng/ml and the set of instructions can then calculate and cause the device to administer the active agent at an initial dosage rate of 1800 µg/hour for an initial period of 5 hours and then lower the dosage rate to a maintenance dosage rate of 540 µg/hour for 7 hours. Similarly, the apparatus may be designed to allow the user to select a steady state concentration of 5 ng/ml and the set of instructions can then calculate and cause the device to administer the active agent at an initial dosage rate of 450 µg/hour for an initial period of 5 hours and then lower the dosage rate to a maintenance dosage rate of 135 µg/hour for 7 hours.

In the embodiments of the invention that allow user input, the apparatus comprises a user interface for user input that permits the user to set the apparatus as desired. The user interface may be an interactive, computer-controlled interface that prompts the user for input. Alternatively, the user interface may be a manual, switch-operated interface.

In embodiments, the apparatus further comprises a monitoring unit capable of adjusting the control unit to achieve the target steady state blood plasma concentration.

In a third aspect, the present invention provides a peptide derived from atrial natriuretic peptide (ANP) prohormone or a mimetic thereof for use in the treatment of a disease in a subject, wherein said peptide or mimetic thereof is administered subcutaneously in a multimodal dosage regime comprising at least an initial dosage stage and at least one maintenance dosage stage, the initial dosage stage comprising infusing the peptide or mimetic thereof at an initial dosage rate for an initial period to achieve a target steady state blood plasma concentration of the peptide or mimetic thereof or metabolite thereof, and the maintenance dosage stage(s) comprising adjusting the dosage rate to a maintenance dosage rate for a maintenance period to substantially maintain said target steady state blood plasma concentration of the peptide or mimetic thereof or metabolite thereof.

In a fourth aspect, the present invention provides a method of treating a cardio-renal syndrome or cancer in a human subject, said method comprising administering subcutaneously to the subject an effective amount of an active agent comprising a peptide derived from atrial natriuretic peptide (ANP) prohormone or a mimetic thereof in a multimodal dosage regime comprising at least an initial dosage stage and at least one maintenance dosage stage, the initial dosage stage comprising infusing the active ingredient at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof.

The methods and uses described herein may be used in conjunction with a diagnostic test for determining the blood plasma concentration of the peptide derived from atrial natriuretic peptide (ANP) prohormone or a mimetic thereof. The results of the test can then be used to alter the dosage rate during the course of treatment to assist in maintaining the target steady state blood plasma concentration. The diagnostic test may be a companion diagnostic which is a privately used device that has one or more disposable components for point-of-care and/or in-home use.

Thus, in a fifth aspect the present invention provides a diagnostic test comprising obtaining a test sample of blood from a subject, determining the blood plasma concentration of the peptide derived from atrial natriuretic peptide (ANP) prohormone or a mimetic thereof, and providing information on the blood plasma concentration. Preferably, the method further comprises using the results of the blood plasma concentration to adjust the dosage rate during administration of the peptide derived from atrial natriuretic peptide (ANP) prohormone or a mimetic thereof to the subject.

The test sample is preferably a blood sample taken from a subject using methods known in the art.

The step of determining the blood plasma concentration of the peptide derived from atrial natriuretic peptide (ANP) prohormone or a mimetic thereof can be performed by protein assay methods. Suitable protein assay methods are known in the art and comprise, for example, immunoassays involving binding of a labelled binding agent to the peptide derived from atrial natriuretic peptide (ANP) prohormone or a mimetic thereof, proteomic based or "protein chip" assays, fibre optic in-situ assays, and the like.

The labelled binding agent may be, for example, an antibody, antibody fragment, protein, aptamer or small-molecule binding agent.

Immunoassays can be conducted using any format known in the art, such as, but not limited to, a sandwich format, a competitive inhibition format (including both forward or reverse competitive inhibition assays) or in a fluorescence polarization format.

Thus, the present invention also provides a method of monitoring the blood plasma levels of a peptide derived from atrial natriuretic peptide (ANP) prohormone or a mimetic thereof in order to optimise dosing or scheduling, the method comprising:

(i) contacting a test blood sample obtained from a subject with a first capture binding agent that binds to the peptide derived from atrial natriuretic peptide (ANP) prohormone or a mimetic or fragment thereof to form a first capture binding agent-peptide complex;
  (ii) contacting the first capture binding agent-peptide complex with a second detection binding agent that binds to the peptide derived from atrial natriuretic peptide (ANP) prohormone or a mimetic or fragment thereof and is conjugated to a detectable label to form a detection-capture binding agent-peptide complex;

(iii) determining the amount of the detection-capture binding agent-peptide complex formed by detecting the detectable label, wherein the amount of the detection-capture binding agent-peptide complex formed is the amount of the peptide derived from atrial natriuretic peptide (ANP) prohormone or a mimetic thereof contained in the test sample; and (iv) comparing the amount of the peptide derived from atrial natriuretic peptide (ANP) prohormone or a mimetic thereof in the test sample determined in step (iii) with a desired blood plasma level.

In some embodiments the method comprises: i) providing a substrate comprising the first capture binding agent that binds to the peptide derived from atrial natriuretic peptide (ANP) prohormone or a mimetic thereof; ii) contacting the substrate with the test sample, iii) exposing the substrate to the second detection binding agent under conditions in which the binding agent-peptide complex is bound by the detection binding agent, and iv) detecting the binding of the detection binding agent to the binding a agent-peptide complex.

The binding agent may be a suitable antibody, antibody fragment, protein, aptamer or small-molecule binding agent that binds to the peptide derived from atrial natriuretic peptide (ANP) prohormone or a mimetic thereof can be used. Monoclonal antibodies are preferred.

The binding agent-peptide complexes formed in the assay can be detected using any suitable technique. Any suitable label can be used. The label must be capable of producing a detectable signal either by itself or in conjunction with one or more additional substances. Useful detectable labels, their attachment to binding agents and detection techniques therefore are known in the art. For example, the detectable label can be a radioactive label, such as $^{3}H$, $^{125}I$, $^{35}S$, $^{14}C$, $^{32}P$, $^{33}P$, an enzymatic label, such as horseradish peroxidase, alkaline peroxidase, glucose 6-phosphate dehydrogenase, etc., a chemiluminescent label, such as, acridinium derivatives, luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label.

The detectable label can be bound to the binding agent either directly or through a coupling agent. An example of a coupling agent that can be used is EDAC (1-ethyl-3-(3-dimethylaminopropyl) carbodiimide, hydrochloride) that is commercially available from Sigma-Aldrich (St. Louis, Mo.). Other coupling agents that can be used are known in the art. Methods for binding a detectable label to binding agents such as antibodies are known in the art.

After formation of the detection-capture binding agent-peptide complex, the amount of label in the complex is quantified using techniques known in the art. For example, if an enzymatic label is used, the labelled complex is reacted with a substrate for the label that gives a quantifiable reaction such as the development of colour. If the label is a fluorescent label, the label is quantified by stimulating the label with a light of one colour (which is known as the "excitation wavelength") and detecting another colour (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. For solution phase immunoassays, once the amount of the label in the complex has been quantified, the concentration of peptide in the test sample is determined by use of a standard curve that has been generated using serial dilutions of the peptide of known concentration. Other than using serial dilutions of the peptide, the standard curve can be generated gravimetrically, by mass spectroscopy and by other techniques known in the art.

Preferably, the assays are carried out in a lab-on-a-chip device and system.

The companion diagnostic test can be used with any of the methods and uses described herein. The test may be particularly useful in conjunction with the apparatus whereby the information on the blood plasma concentration that is provided by the diagnostic test is fed back to the apparatus. This could be manual or electronic feedback. A processor in the apparatus can be programmed to adjust the flow rate depending on the blood plasma concentration identified by the test. For example, if the amount of the peptide derived from atrial natriuretic peptide (ANP) prohormone or a mimetic thereof detected in the test sample is less than the desired level the information may be fed back to the apparatus and the processor may increase the dosage rate accordingly.

Data we have obtained from subjects administered the peptide derived from atrial natriuretic peptide (ANP) prohormone or a mimetic thereof shows that urine output and urinary sodium excretion increases after administration of the peptide. Without intending to be bound by a specific theory, we propose that the peptide derived from atrial natriuretic peptide (ANP) prohormone or a mimetic thereof increases $Na^+$ secretion and water elimination in subjects treated with the peptide and, resulting in a concomitant improvement in renal function and also in cardiac function. As is known in the art, renal function can be monitored by determining the concentration of at least one renal function biomarker in a body fluid, such as blood or urine. Thus, a change in the concentration over time of at least one renal function biomarker in a body fluid of subjects treated with the peptide derived from atrial natriuretic peptide (ANP) prohormone or a mimetic thereof may be used as an indicator of the efficacy of the treatment. Accordingly, in a seventh aspect, the present invention provides a method of optimising dosing of an active agent comprising a peptide derived from atrial natriuretic peptide (ANP) prohormone or a mimetic thereof to a subject, the method comprising:

(i) administering subcutaneously to the subject an effective amount of the active agent in a multimodal dosage regime comprising at least an initial dosage stage and at least one maintenance dosage stage, the initial dosage stage comprising infusing the active agent at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof;

(ii) determining the concentration of at least one renal function biomarker in a body fluid of the subject at two or more time points;

(iii) comparing the concentrations of the at least one renal function biomarker at the two or more time points to ascertain whether renal function of the subject has improved over time;

(iv) using the data obtained from step (iii) to determine whether the dosage rate of the active agent should be adjusted; and (v) if necessary, adjusting the dosage rate of the active agent during the initial dosage stage and/or the maintenance dosage stage(s) based on the determination made at step (iv).

Any of the renal function biomarkers known in the art can be used, including creatinine, urea, and electrolytes as an indicator of renal function. Alternatively, or in addition, markers such as inulin or sinistrin may be injected into the plasma of a subject and the glomerular filtration rate (GFR) can be measured over time and the measurement used as an indicator of renal function (Israni et al., 2011).

In specific embodiments, the concentration of creatinine in a body fluid of the subject is measured over time. In these embodiments, the body fluid may be blood or urine. An increase in the concentration of creatinine in the body fluid of the subject over time indicates impairment of renal function whereas a decrease in the concentration of creatinine in the body fluid of the subject over time indicates an improvement of renal function. In embodiments, the rate of change in the concentration of creatinine in the body fluid of the subject over time can be used to adjust the dosage rate of the active agent. For example, the dosage rate of the active agent may be increased if the creatinine clearance rate has not decreased at a desired rate over a predetermined period of time.

The present invention also provides an infusion device when used in accordance with the method of the fourth aspect of the invention.

EXAMPLES

The invention is hereinafter described by reference to the following non-limiting examples and accompanying figures.

Example 1

Formulation

VSDL in the form of a white lyophilised powder (synthesised using standard protein synthesis method by Auspep Pty Ltd, Parkville, VIC, Australia), stored in an ultra low freezer (−80° C.), was reconstituted in a vial with 10 ml of 0.9% saline (preservative free) and aseptically transferred into a 20 ml syringe (that connects to a patient cannula) before use.

Study Population

Test adult subjects, both male and female, showing either acute exacerbations of chronic CHF or ADCHF (ie in individuals who had not previously shown heart failure), were recruited for the study. All subjects used in these studies also underwent existing standard of care treatments for the condition for which they presented. These treatments were typically diuretic therapy (eg loop diuretic especially furosemide) and an antihypertensive drug (eg an Angiotensin Converting Enzyme (ACE) inhibitor).

A cohort of 10 subjects with stable CHF and undergoing standard of care treatment was treated with the formulation as follows:
  i) 2 sentinel subjects were treated with a one stage 6 hour sc infusion of VSDL at 900 µg/h (Subjects 1 and 3)
  ii) 5 subjects were treated with a one stage 12 hour sc infusion of VSDL at 900 µg/h (Subjects 102, 103, 104, 105 and 106); and
  iii) 3 subjects were treated with a bimodal sc infusion of VSDL at 900 µg/h for 5 hours and then 550 µg/h for 7 hours (Subjects 111, 112 and 114).

Dose Regimen

The dose regimen for this trial was designed using a pharmacokinetic model for VSDL based on prior data.

The final model was used to simulate the median and 90% prediction intervals for 1000 patients given VSDL at 900 µg/h for 5 h then 550 µg/h for 7 h. This dose regimen targeted a population value of 10 ng/ml for the period 6-12 h after the start of the infusion.

The predictions of the model were compared to observed VSDL concentration data from the three subjects referred to at iii) above.

Results

The parameters of the pharmacokinetic model are shown in Table 1.

TABLE 1

| Parameter | Description | Pop value | Unit | se (%) | BSV | Unit | se (%) |
|---|---|---|---|---|---|---|---|
| CL | Clearance | 15.8 | L/h | fixed | 39.66 | % | 32.86 |
| V | Central volume | 8.93 | L | 8.00 | 46.49 | % | 35.28 |
| LGT1 | Logit F value | −1.05 | | 11.80 | 0.77 | additive | 43.47 |
| F | Bioavailability | 0.259 | . | . | . | . | . |
| KA | Absorption rate constant | 0.265 | 1/h | 19.80 | 49.92 | % | 27.07 |
| V2 | Multiplier of V for sc bolus | 1.596 | . | 37.8 | | | |
| V3 | Multiplier of V for sc infusion | 3.142 | . | 27.1 | | | |
| KARATE | Effect of infusion rate of KA | −0.135 | . | 20.2 | | | |
| KAVOL | Effect of infusion volume on KA | 0.222 | . | 58.9 | | | |
| RUVCV | Residual Error (Proportional) | 0.234 | Ratio | 13.36 | . | . | . |
| RUVADD | Residual Error (Additive) | 0.071 | ng/ml | 26.05 | . | . | . |

Refined parameters of the pharmacokinetic model are shown in Table 2.

TABLE 2

| Parameter | Description | Pop value | Unit | se (%) | BSV | Unit | se (%) |
|---|---|---|---|---|---|---|---|
| CL | Maximum Elimination rate | 26.8 | L/h | 15.3 | 56.70 | % | 52.20 |
| V | Central volume | 13.20 | L | 20.40 | 56.70 | % | 52.20 |
| V2 | S.C. bolus V scaling factor | 1.62 | ratio | 49.1 | | | |
| V3 | S.C. infusion V scaling factor | 3.65 | ratio | 11.5 | | | |
| KA | Absorption rate constant | 0.625 | 1/h | 17.90 | 38.60 | % | 164.40 |
| LGT | Logit F value | −1.00 | . | 281.00 | 1.46 | . | 54.20 |
| F | Bioavailability | 26.894 | % | . | . | . | . |
| FVOL | Infused volume on F | 1.590 | ratio | 24.8 | | | |

TABLE 2-continued

| Parameter | Description | Pop value | Unit | se (%) | BSV | Unit | se (%) |
|---|---|---|---|---|---|---|---|
| ETASHARE | Random effect scalinmg factor | 1.000 | ratio | 8.8 | . | . | . |
| RUVCVIV | Residual Error (Proportional, I.V.) | 0.336 | ratio | 22.00 | . | . | . |
| RUVADDIV | Residual Error (Additive, I.V.) | 0.248 | ng/ml | 28.70 | . | . | . |
| RUVCVSC | Residual Error (Proportional, S.C.) | 0.259 | Ratio | 18.20 | . | . | . |
| RUVADDSC | Residual Error (Additive, S.C.) | 0.070 | ng/ml | 95.60 | . | . | . |

Source: E:\a-jobs\Madeleine\NM14\base_ETAshare_splitRUV.nm7\[base_ETAshare_splitRUV.smr.format.xlsx]Sheet 1
Pop value + typical value in population; BSV = between subject variability; RUV = residual unexplained variability; se = standard error of parameter estimate (uncertainty), wherein se determined via importance sampling.

Figure 2:
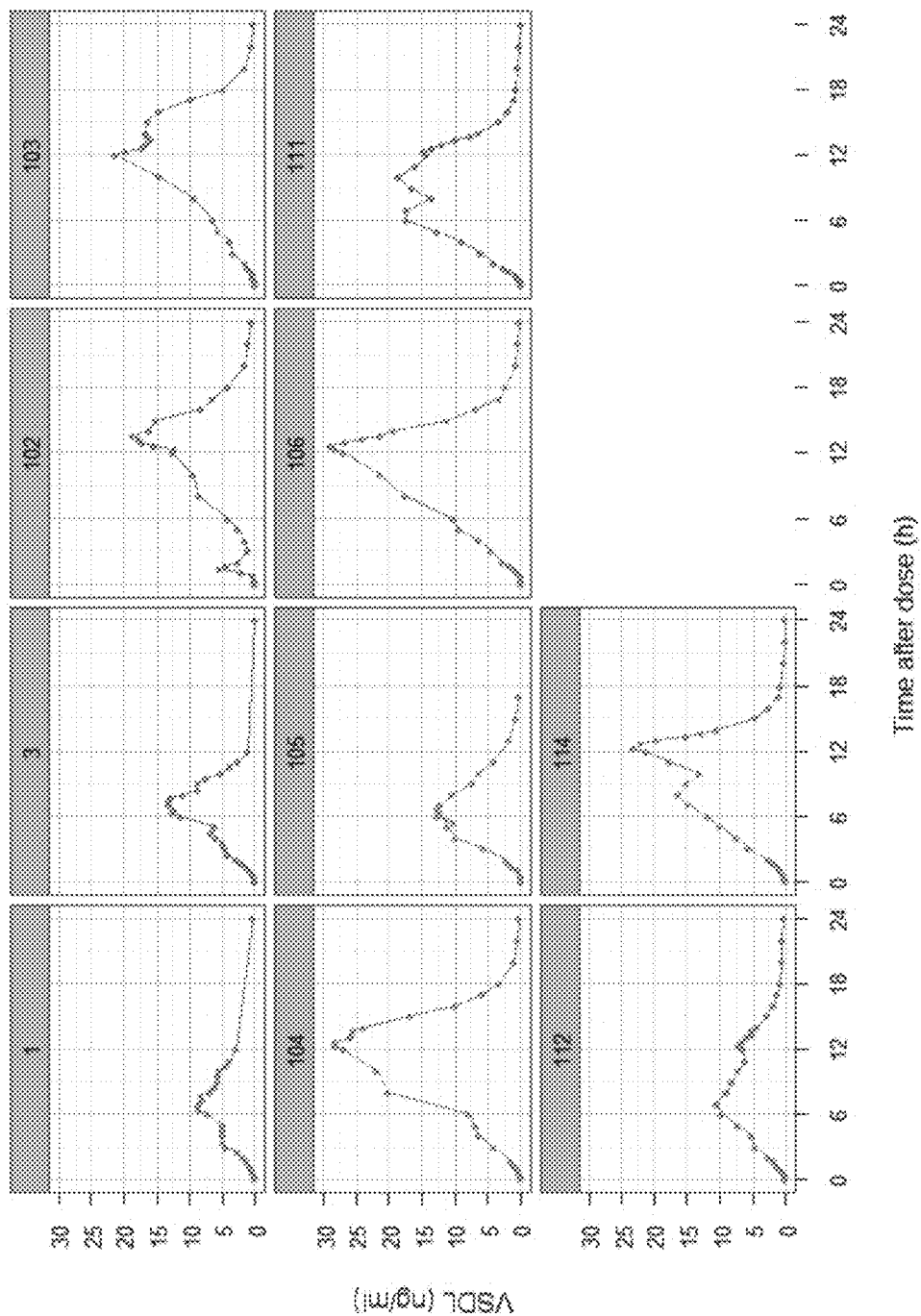
FIG. 2 shows individual plots of time (h) after dose vs blood plasma VSDL concentration (ng/ml) observed for all subjects. The titles of each plot refer to the subject number.

The actual and predicted VSDL plasma concentrations are shown in FIG. 1 and the observed data is shown in FIG. 2.

Patients 111 and 114 had concentrations in the 6-12 h window at the upper level of predictions (FIG. 1; grey ribbon).

Patient 112 had concentrations in the 6-12 h window at the lower level of predictions (FIG. 1; grey ribbon).

Only Patient 111 appeared to be at steady-state in the 6-12 h window.

The post-infusion concentrations declined quicker than model predictions, as the new patients appeared to have a shorter period of sustained concentrations once the infusion was stopped.

Figure 3:
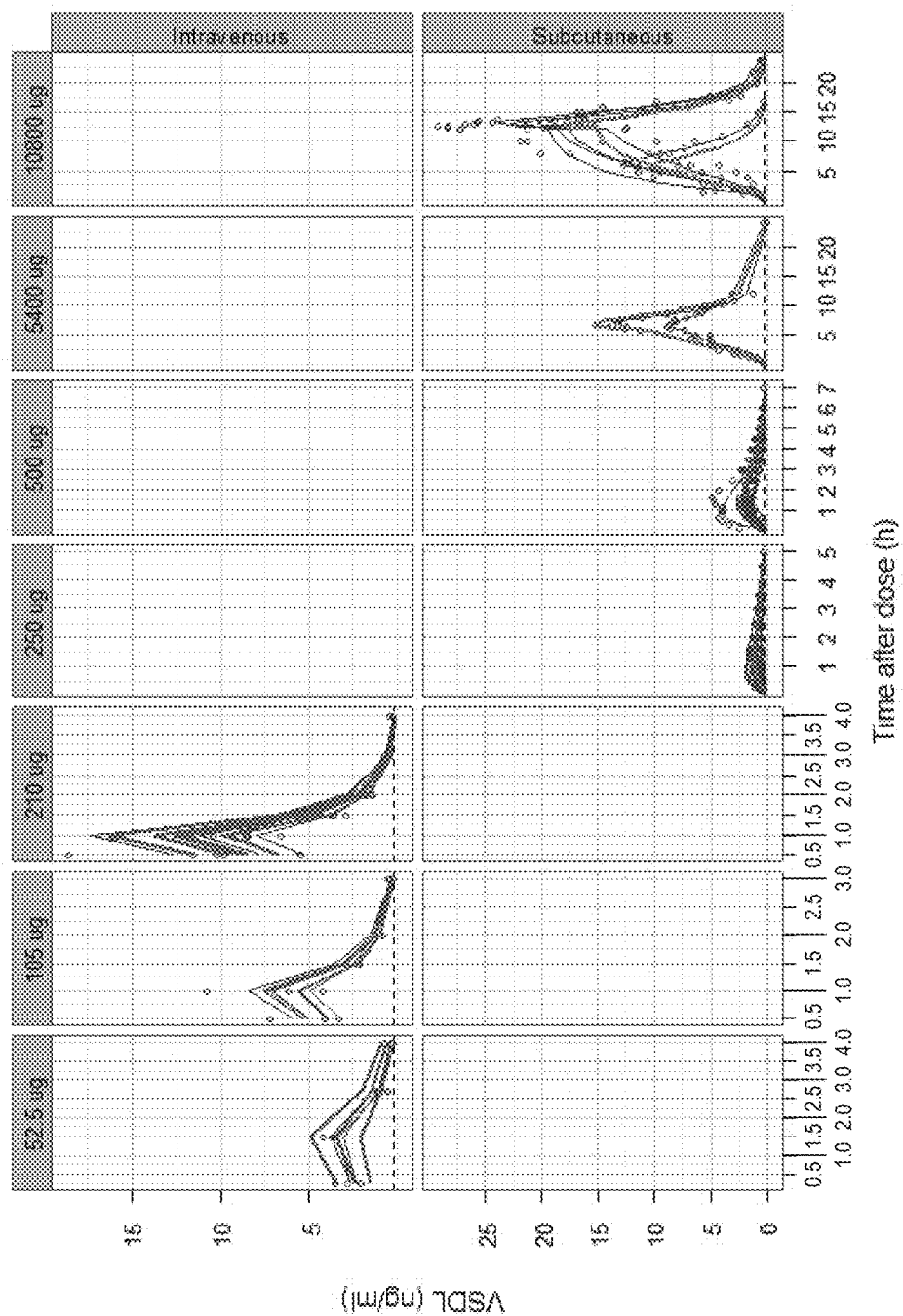
FIG. 3 shows plots of time (h) after dose vs blood plasma VSDL concentration (ng/ml) observed at doses of 52.5 µg, 105 µg, 210 µg, 250 µg, 500 µg, 5400 µg, and 10800 µg. The symbols are the observed data and the lines are the population predicted data.
Figure 4:
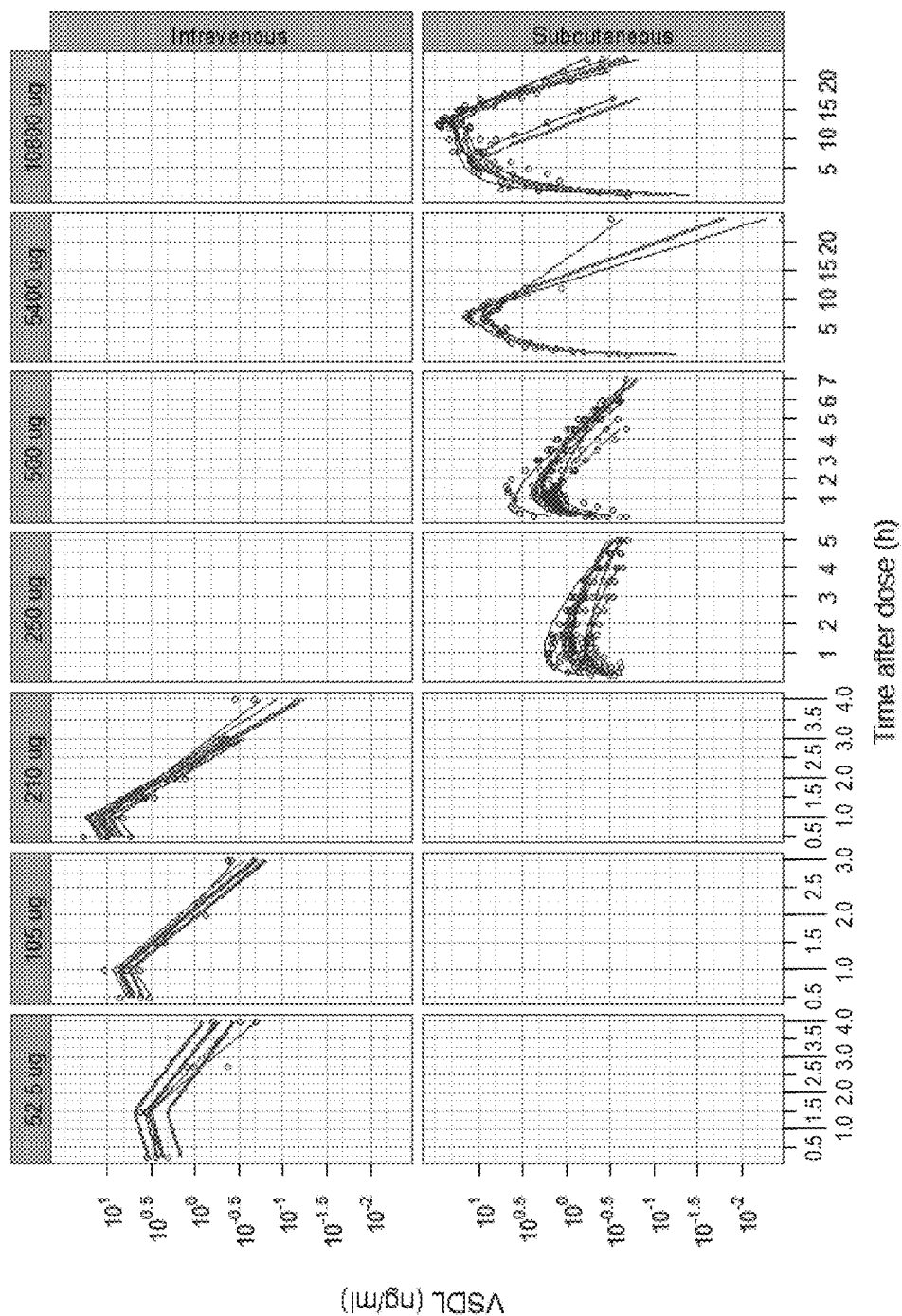
FIG. 4 shows plots of time (h) after dose vs blood plasma VSDL concentration (ng/ml) observed at doses of 52.5 µg, 105 μg, 210 μg, 250 μg, 500 μg, 5400 μg, and 10800 μg. The symbols are the observed data and the lines are the population predicted data.

The observed and individual predicted VSDL concentrations are shown in FIGS. 3 and 4 in which the data labeled MADE03 is from the present study.

A model where infusion rate (ml/h) and delivered volume (ml) affected KA was an acceptable empirical description of the data. This model reproduced the observed increase in VSDL concentrations at the end of a subcutaneous infusion. The net effect was generally that KA increased with time during subcutaneous infusions.

Figure 5:
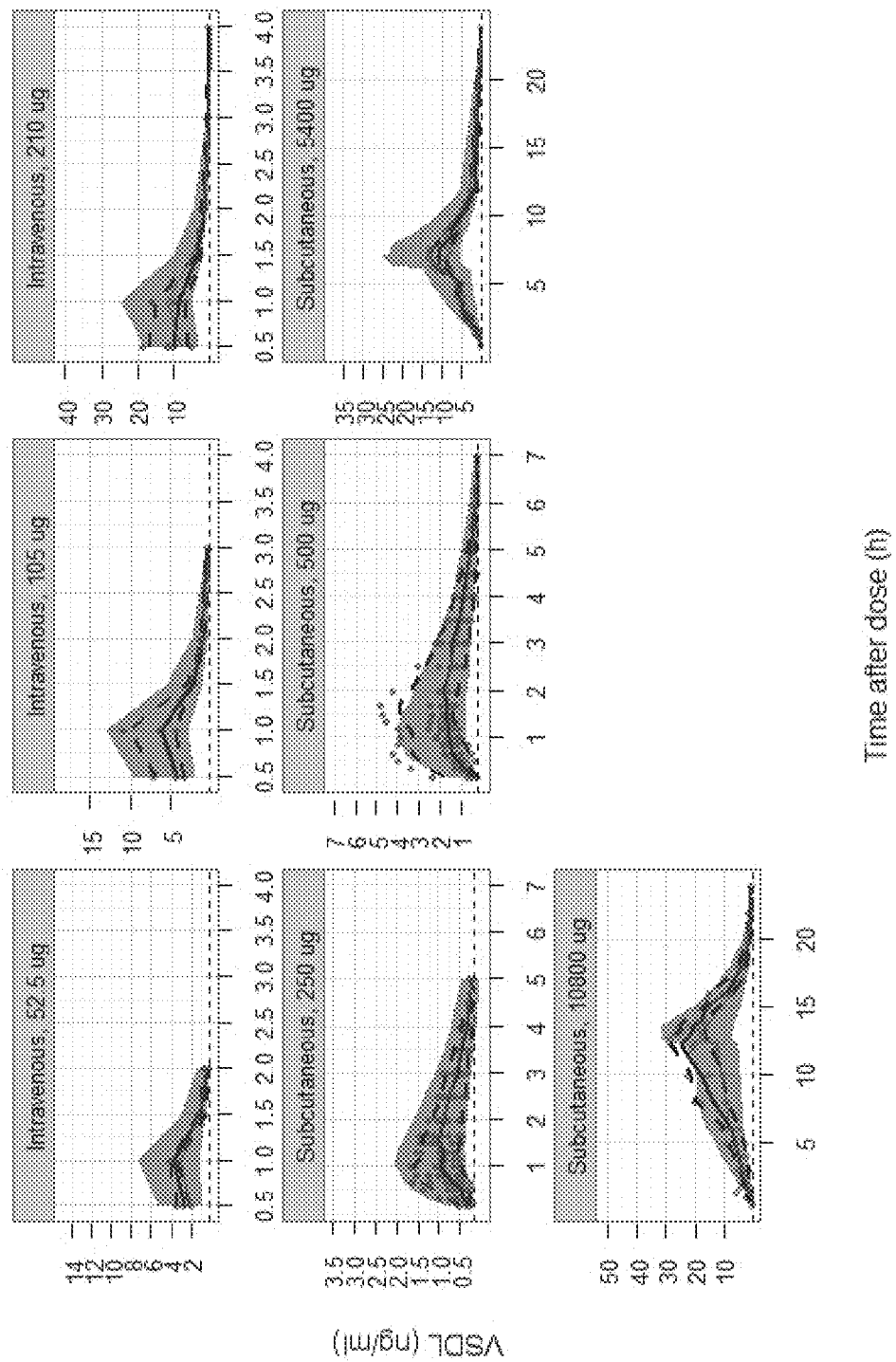
FIG. 5 shows plots showing the results of Visual Predictive Checks of the model used in the study. The observed data is shown with symbols (median) and black lines (90% CI) whilst the simulated data is shown with red lines (median) and ribbon (90% CI). The green symbols show the data from the present study.
Figure 6:
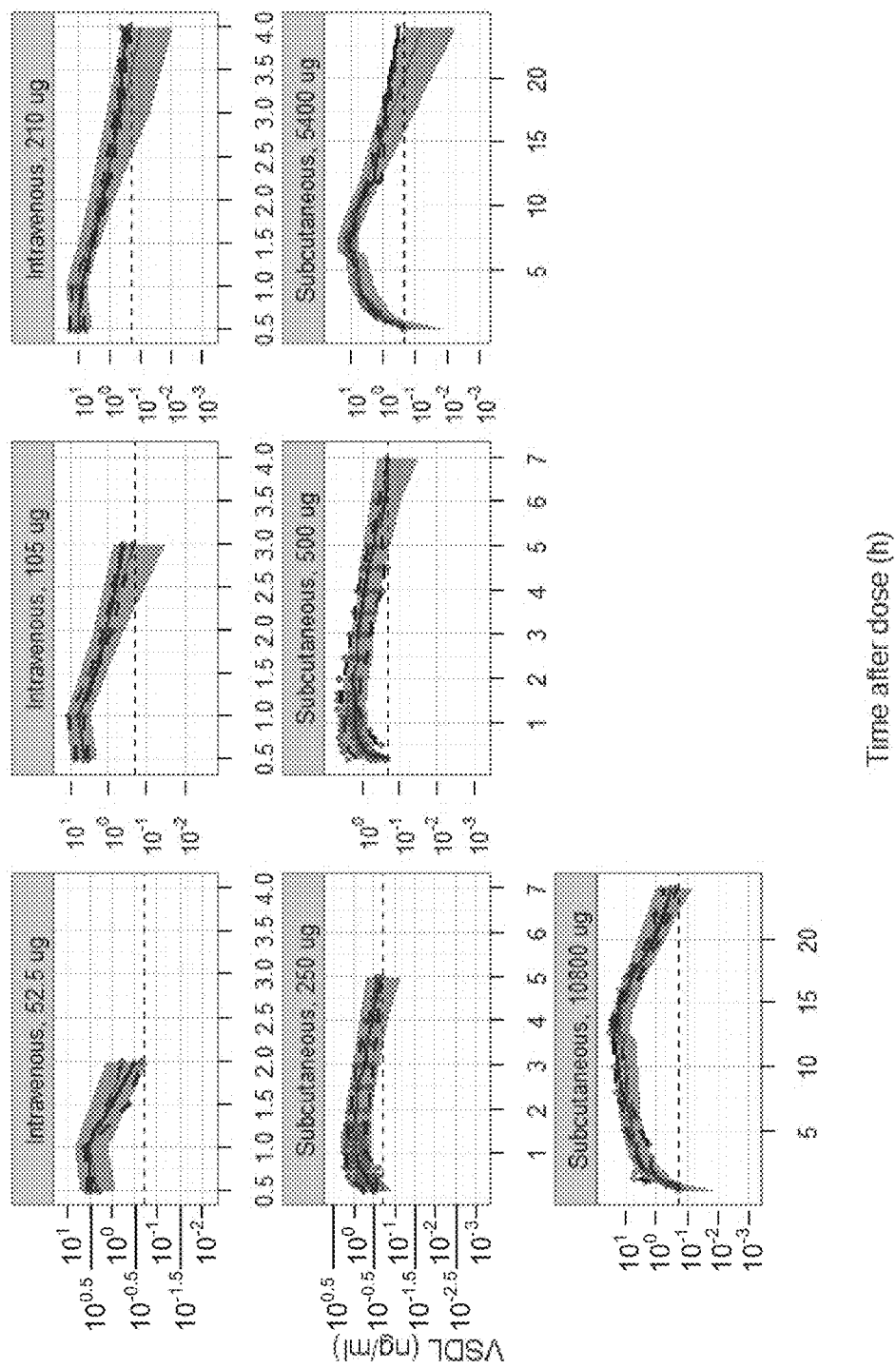
FIG. 6 shows plots showing the results of Visual Predictive Checks of the model used in the study. The observed data is shown with symbols (median) and black lines (90% CI) whilst the simulated data is shown with red lines (median) and ribbon (90% CI). The green symbols show the data from the present study.

The results of Visual Predictive Checks of the final model are shown in FIGS. 5 and 6.

A final model where infusion rate (ml/h) and delivered volume (ml) affected KA was an acceptable empirical description of the data. The final model had acceptable predictive performance based on the Visual Predictive Checks (allowing for low number of subjects).

The final model can be used to design a dose regimen targeting a constant VSDL concentration.

It was observed that the influence of creatinine clearance (CCL) and body mass index (BMI) on VSDL elimination kinetics is minor.

Example 2—Dosing Subjects to Achieve a Target Css of 10 ng/mL

The materials and dosage protocols used in Example 1 were used to treat two patients, 201 and 202. Each subject received sc VSDL at 900 µg/h for 5 h then 550 µg/h for 7 h.

Method

The dose regimen was designed using the pharmacokinetic model discussed in Example 1. The final model was used to simulate the median and 90% prediction intervals for 1000 patients given VSDL at 900 µg/h for 5 h then 550 µg/h for 7 h.

This dose regimen targeted a population value of 10 ng/ml for the period 6-12 h after the start of the infusion.

Figure 7:
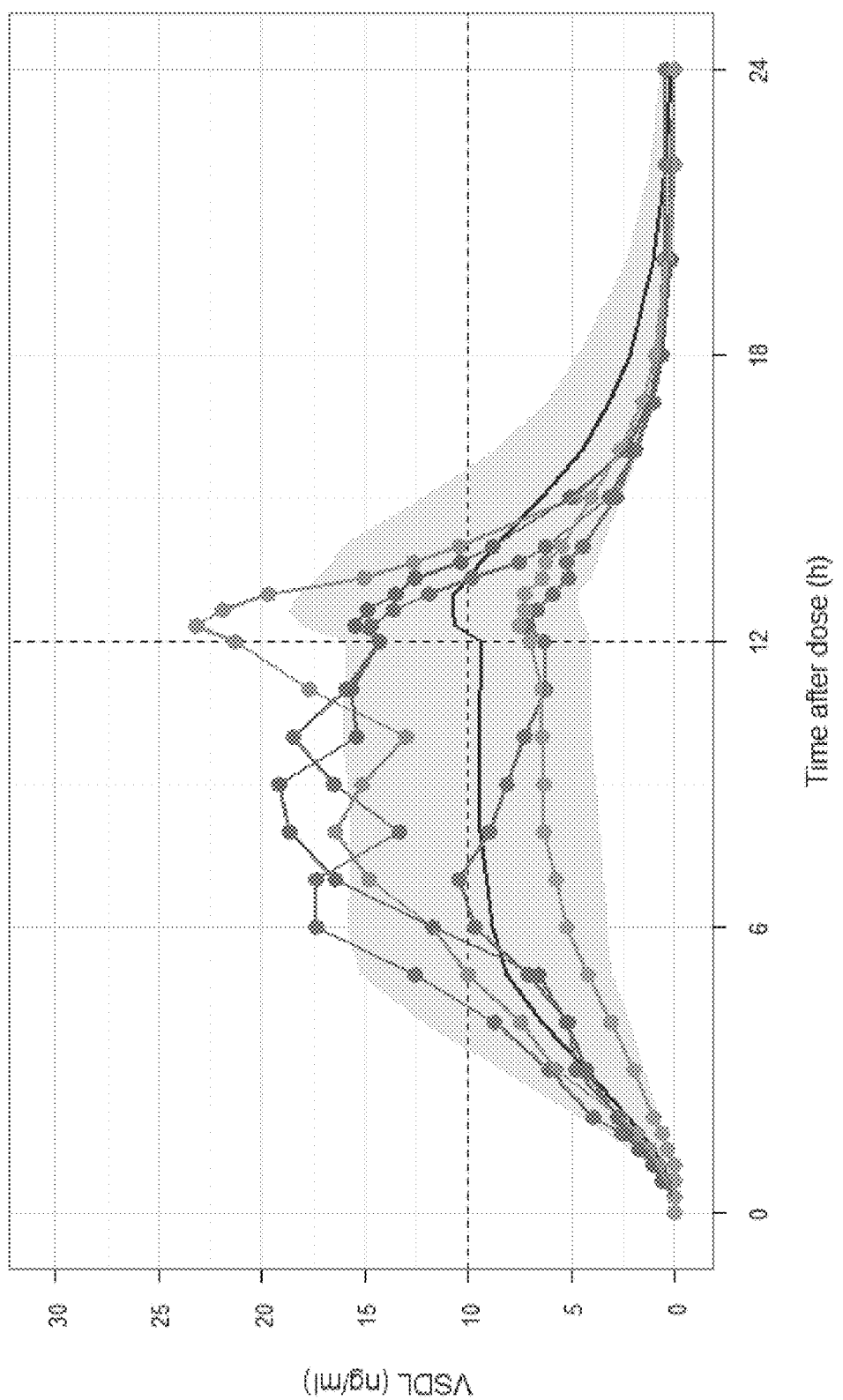
FIG. 7 shows a plot of time (h) after dose vs blood plasma VSDL concentration (ng/ml) for the three subjects from Example 1 and two subjects from Example 2. The black line and ribbon is the mean and 90% CI predicted for 1000 patients and the symbols are the observed data.
Figure 8:
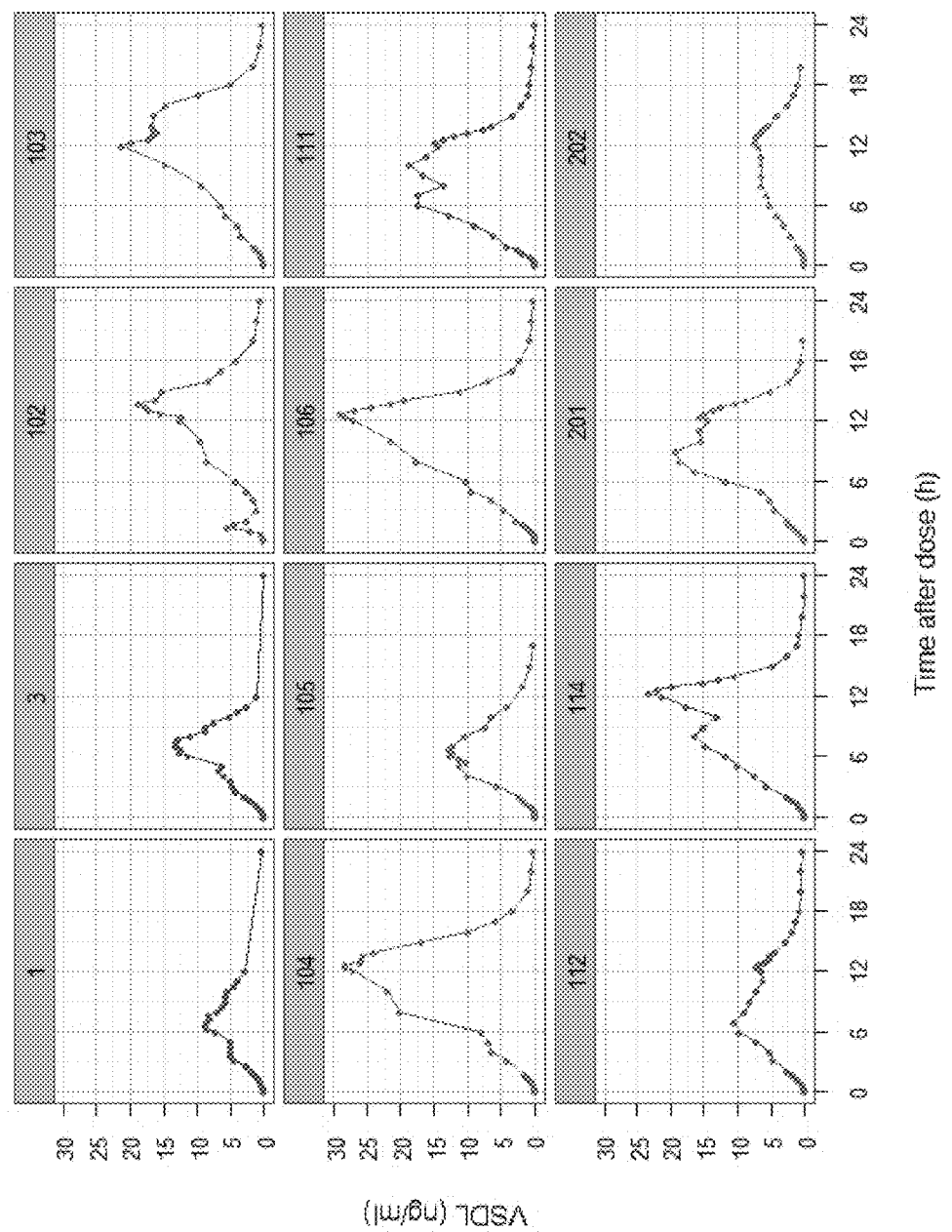
FIG. 8 shows individual plots of time (h) after dose vs blood plasma VSDL concentration (ng/ml) observed for all subjects. The titles of each plot refer to the subject number.
Figure 9:
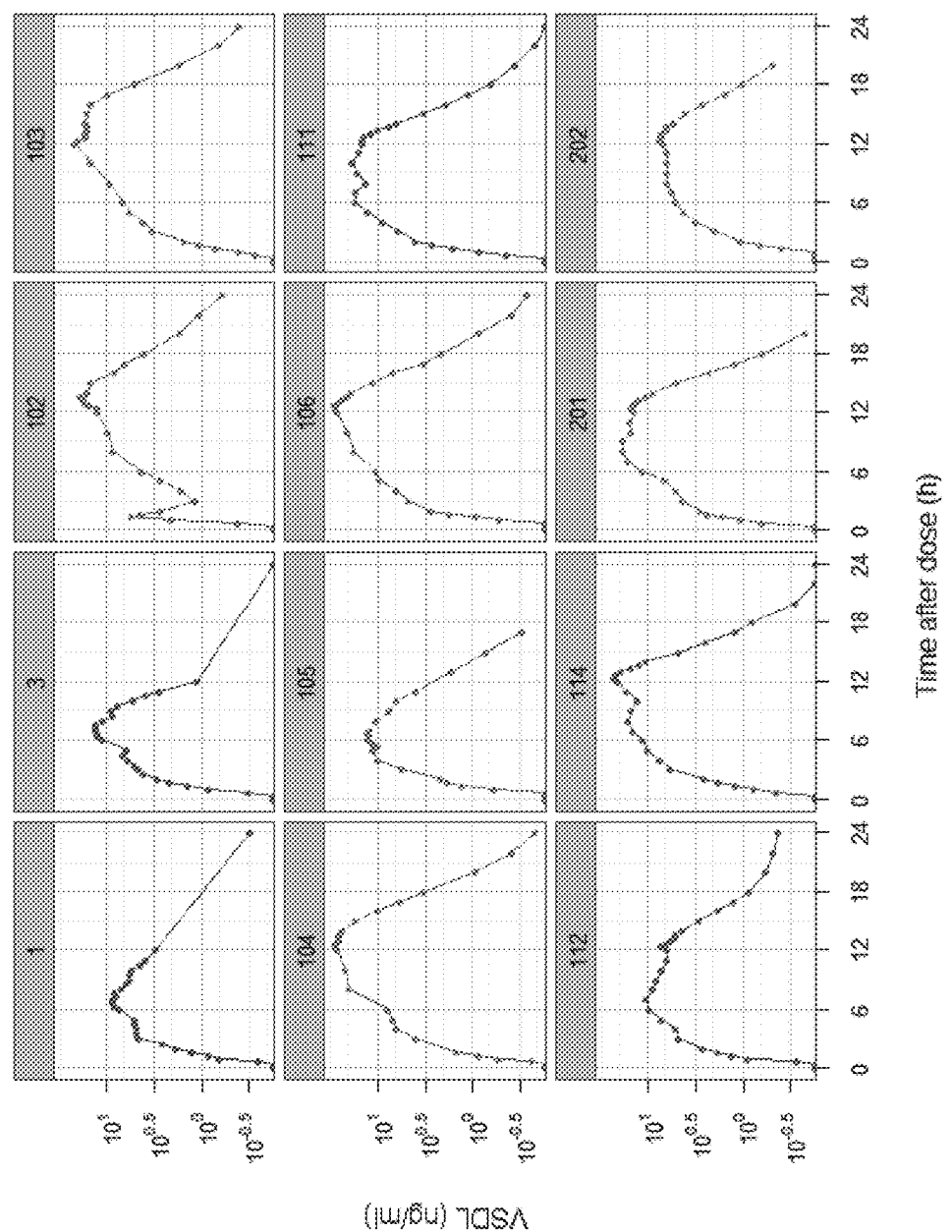
FIG. 9 shows individual plots of time (h) after dose vs blood plasma VSDL concentration (ng/ml) observed for all subjects. The titles of each plot refer to the subject number.

The predictions of the model were compared to observed VSDL concentration data from the two patients and the data are shown in FIGS. 7 to 9.

Example 3—Dosing Subjects to Achieve a Target Css of 20 ng/mL

The materials used in Example 1 were used to treat six subjects (subjects 224-229 and 234). Each subject received sc VSDL at 1800 µg/h for 5 h then 1080 µg/h for 7 h.

Results—Css

Figure 10:
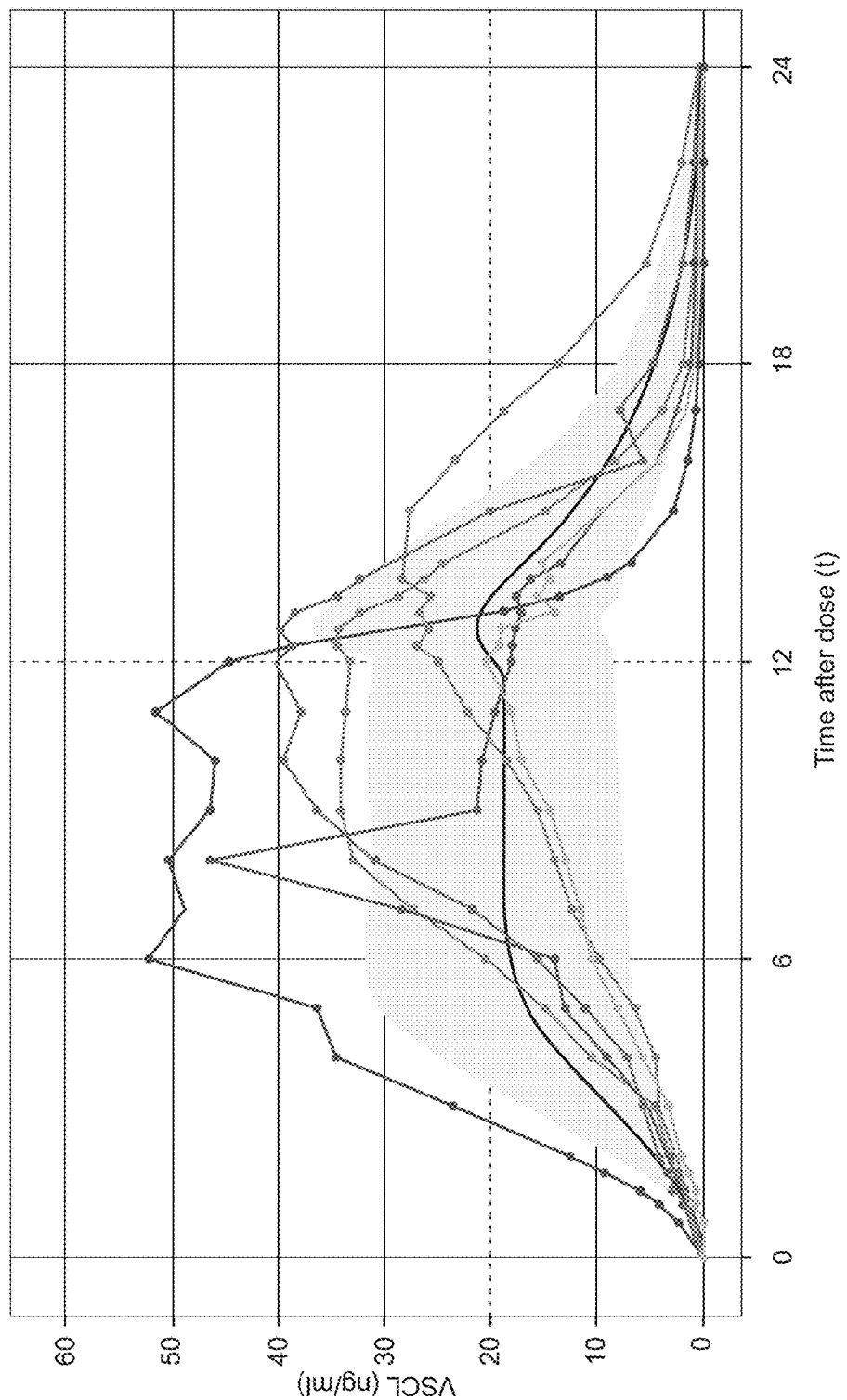
FIG. 10 shows a plot of time (h) after dose vs blood plasma VSDL concentration (ng/ml) for patients eight subjects from Example 3. The black line and ribbon is the mean and 90% CI predicted for 1000 patients and the symbols are the observed data.
Figure 11:
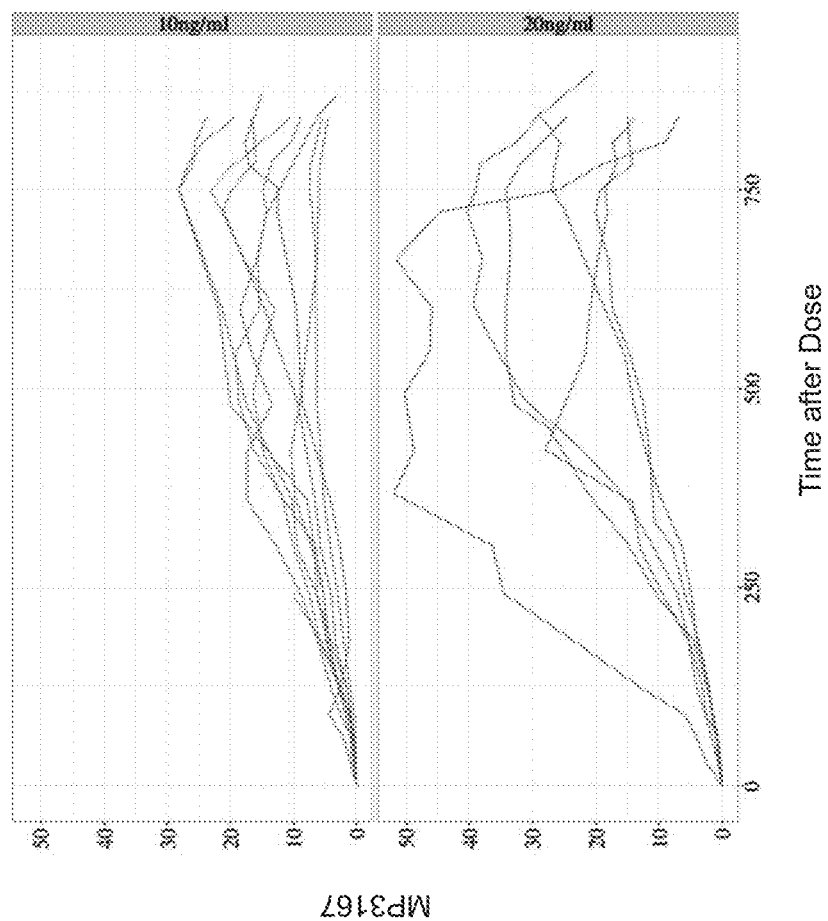
FIG. 11 shows plots of time (h) after dose vs blood plasma VSDL concentration (ng/ml) for subjects from Example 2 (top graph) and subjects from Example 3 (bottom graph).

The observed VSDL concentration data for subjects treated according to Example 3 are shown in FIG. 10. The concentrations of VSDL achieved in subjects treated according to Example 2 (top graph) and Example 3 (bottom graph) are also shown in FIG. 11.

Results—Cardiac Parameters

Figure 12:
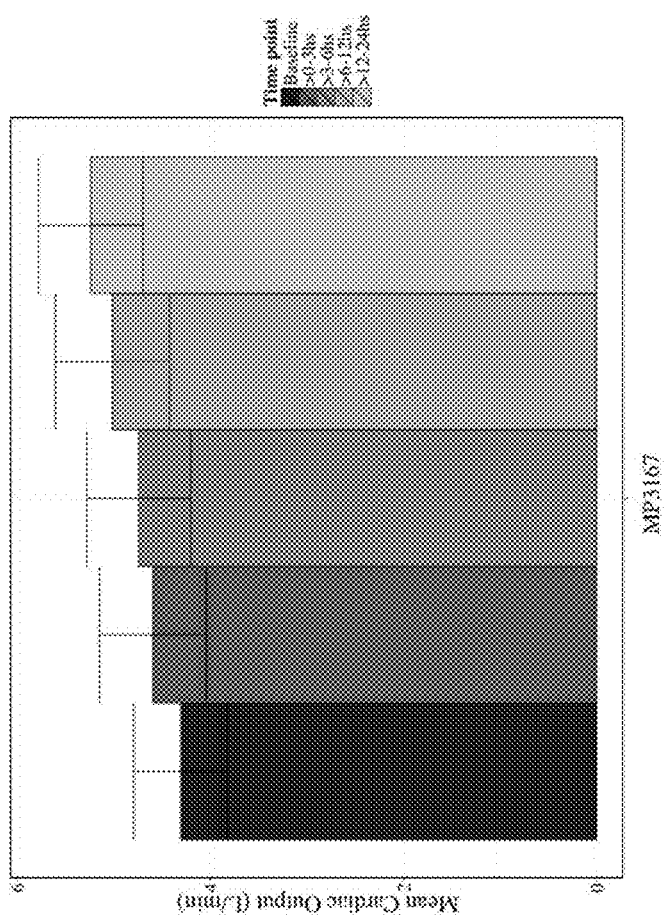
FIG. 12 shows a plot of Mean Cardiac Output in ADCHF and Stable CHF patients over time.

Regression of cardiac output on time accommodating repeated measures demonstrated that patients treated with VSDL had a significant increase in cardiac output which equates to an increase on average of 0.000472 L/min above baseline (t=3.16; p≤0.05) (FIG. 12). Additionally, there were no severe adverse events reported and all reported adverse events were self-limiting, recovering without need for intervention.

Results—Renal Parameters

Figure 13:
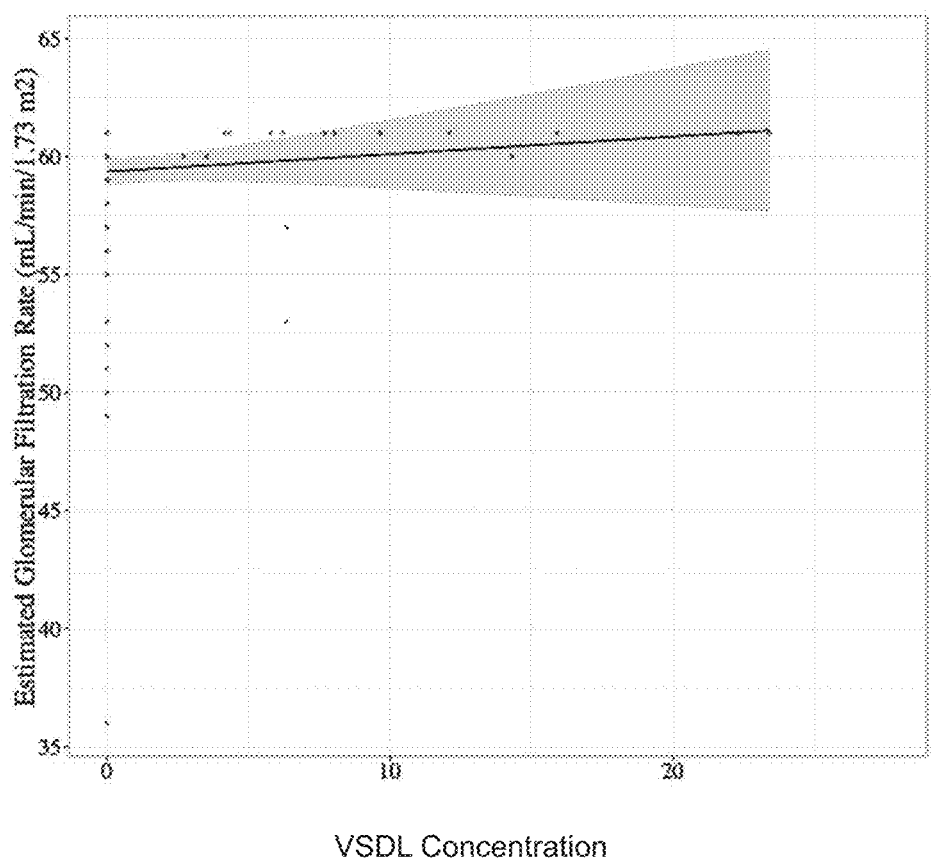
FIG. 13 shows a plot of blood plasma VSDL concentration (ng/ml) vs estimated glomerular filtration rate (mL/min/1.73 m$^2$) for subjects from Example 3.
Figure 14:
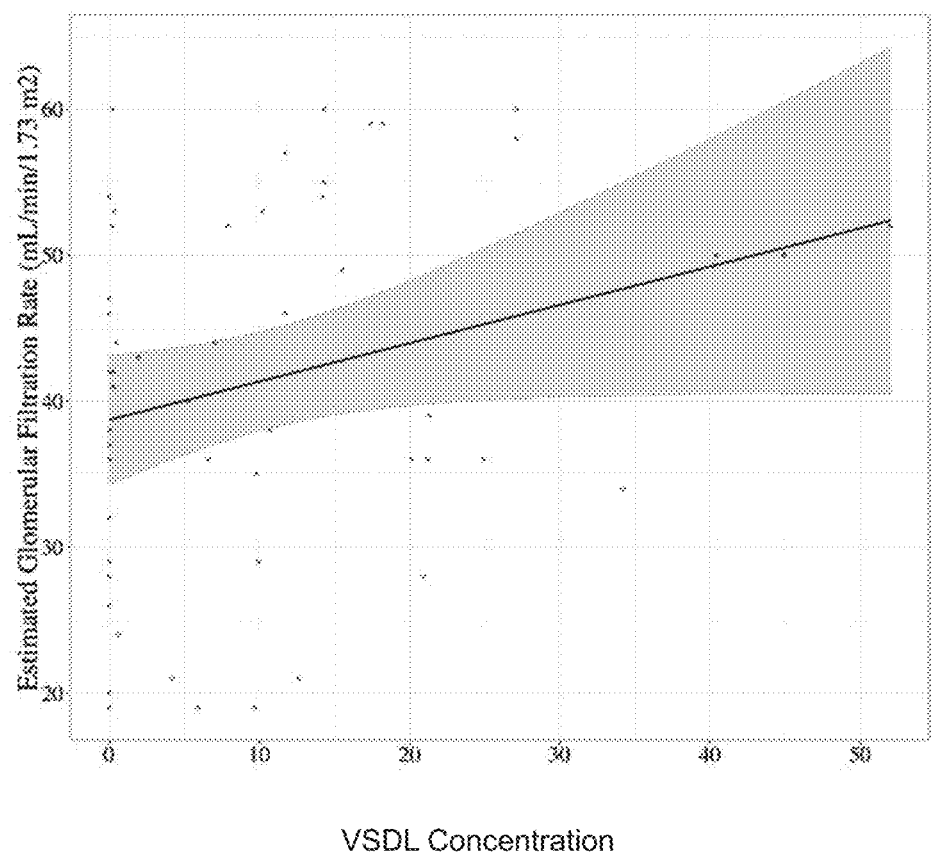
FIG. 14 shows a plot of blood plasma VSDL concentration (ng/ml) vs estimated glomerular filtration rate (mL/min/1.73 m$^2$) for subjects from Example 2.
Figure 15:
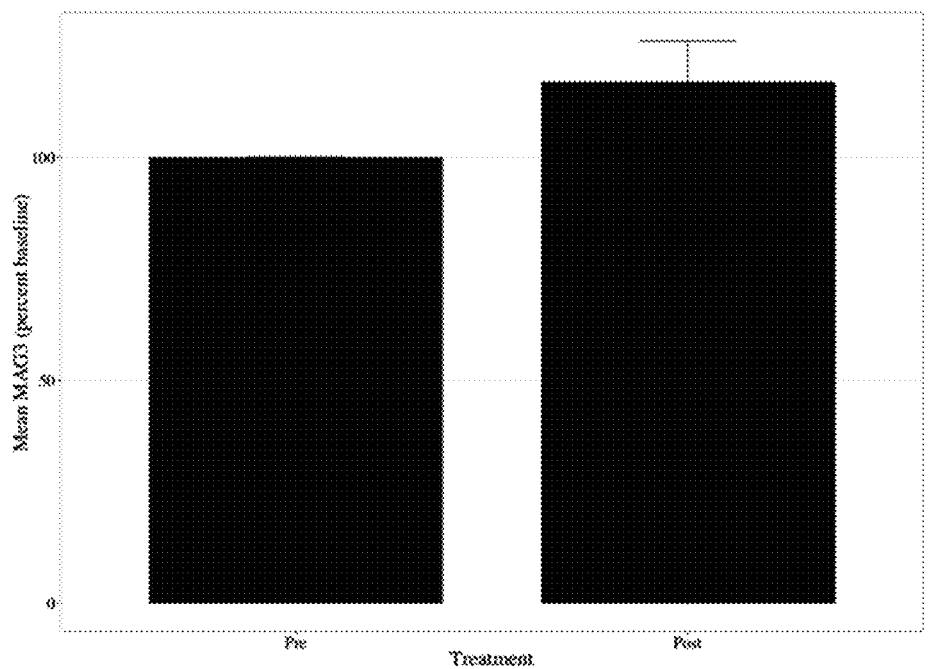
FIG. 15 shows a plot of mean MAG3 clearances (percent baseline) for subjects from Examples 2 and 3 pre- and post-treatment with VSDL.
Figure 16:
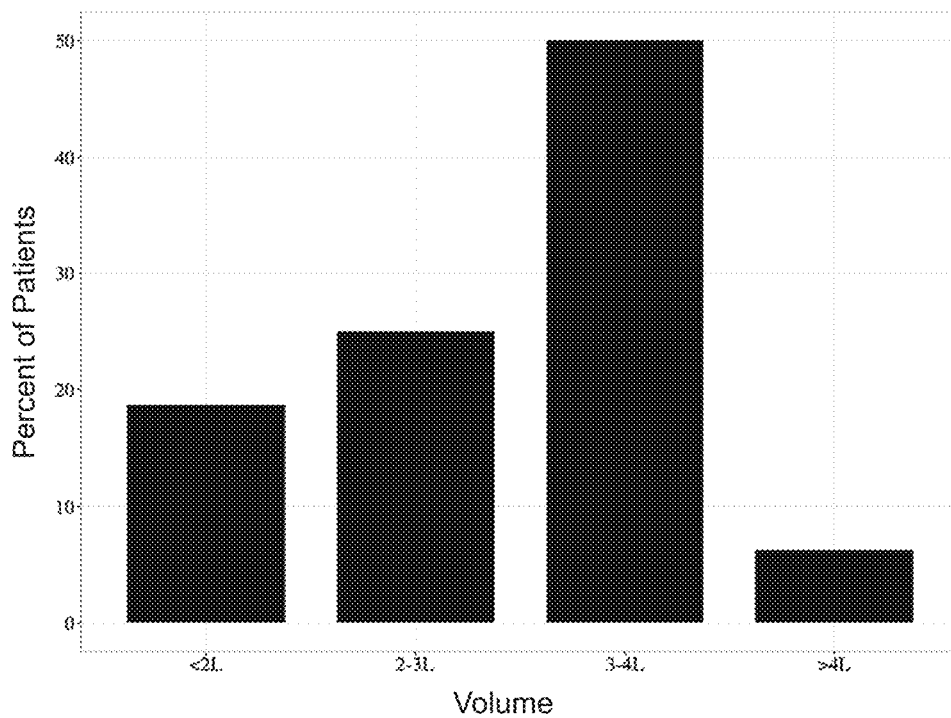
FIG. 16 shows a plot of urine output (L) vs percent of subjects from Examples 2 and 3.
Figure 17:
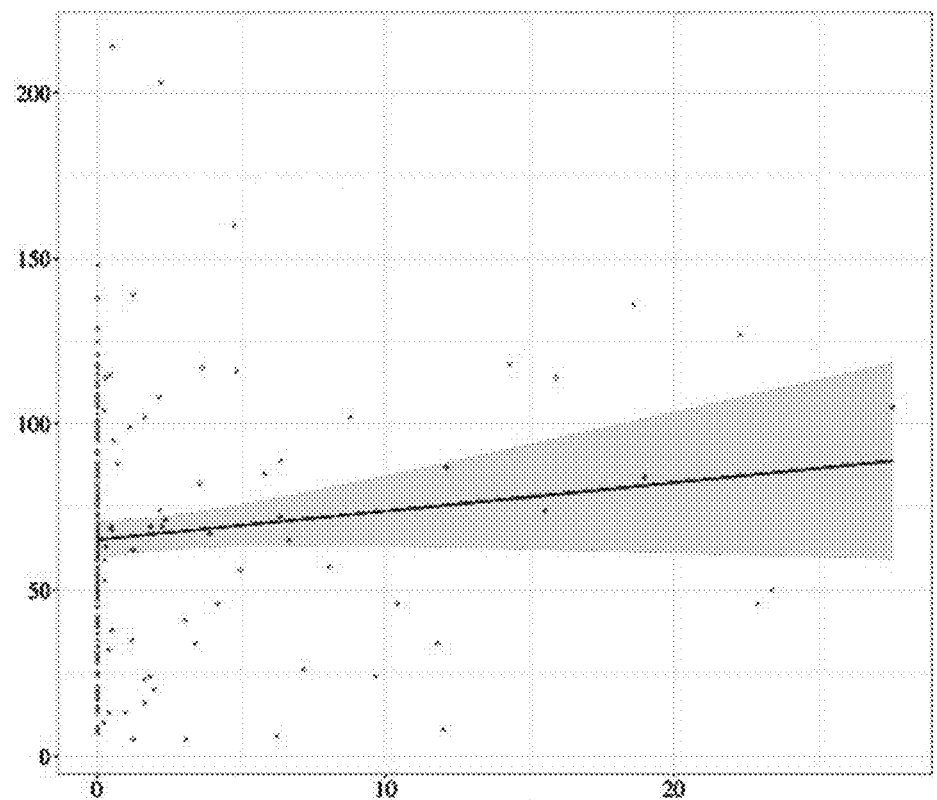
FIG. 17 shows a plot of blood plasma VSDL concentration (ng/ml) vs urine sodium (mEq/L) for subjects from Examples 2 and 3.
Figure 18:
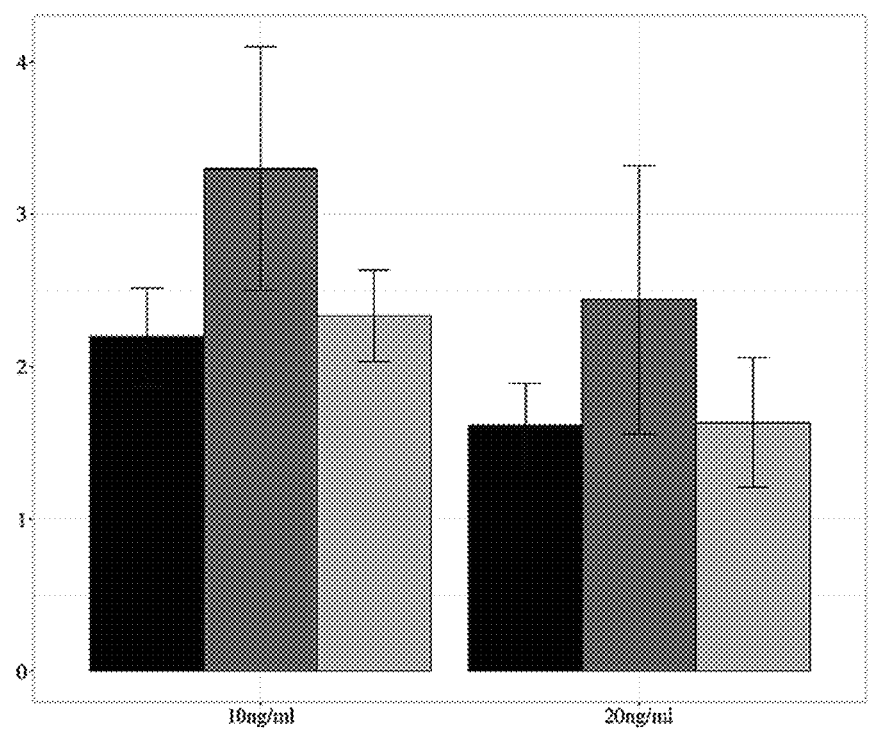
FIG. 18 shows a plot mean FENa (%) for the 10 ng/mL blood plasma VSDL concentration subjects from Example 2 and the 20 ng/mL blood plasma VSDL concentration subjects from Example 3.

There was a significant increase in eGFR in the Stable CHF patient group (Baseline=37±11 mL/min/1.73 m$^2$; 10 ng/kg=42±15 mL/min/1.73 m$^2$; 20 ng/kg=45±9 mL/min/1.73 m$^2$, p≤0.05) (FIG. 13). However, since the patient cohort in the ADCHF included patients with relatively well preserved renal function and since the patient numbers were small the increases in eGFR were not significant but the same trend was also evident in this group (untreated=59±3 mL/min/1.73 m$^2$; treated: 60±2 mL/min/1.73 m$^2$) (FIG. 14). The improvement in renal function was also demonstrated by a 17% increase in 99Tc-MAG3 clearances in the VSDL treated group (FIG. 15). Similarly, there was an increase in 24-hour urine output in the Stable CHF groups (10 ng/kg=2898±335 mls; 20 ng/kg=3028±302 mls) (FIG. 16). This increased urine output was accompanied by an increase of fractional extraction of sodium from 2.2±0.3% at baseline to 3.3±0.8% in the 10 ng/ml group and from 1.6±0.3% to 2.4±0.9% in the 20 ng/ml group at 6-12 hrs post treatments (FIGS. 17 and 18). This concomitant increase in sodium and water excretion demonstrates that the water loss was not due to aberrant water reabsorption. These results indicate a strong renal protective role for VSDL in the setting of congestive heart failure.

Results—Vasodilation

There was a significant drop in systolic and diastolic blood pressures in the stable CHF group (Table 3). However, none of these resulted in symptomatic hypotension.

TABLE 3

Blood Pressures in patients treated with VSDL in Stable Congestive Heart Failure ($p < 0.05$)

|  | Baseline | 10 ng/kg | 20 ng/kg |
| --- | --- | --- | --- |
| Systolic Blood Pressure (mmHg) | 119 ± 15 | 122 ± 10 | 115 ± 19 |
| Diastolic Blood Pressure (mmHg) | 65 ± 10 | 64 ± 7 | 65 ± 6 |

Example 4—Dosing Subjects to Achieve a Target Css of 20 ng/mL

Method

A dose regimen was designed using the pharmacokinetic model discussed in Example 1. The model was used to simulate the median and 90% prediction intervals for 1000 patients given VSDL at 1800 μg/h for 5 h then 540 μg/h for 7 h.

This dose regimen targeted a population value of 20 ng/ml for the period 6-12 h after the start of the infusion.

Figure 19:
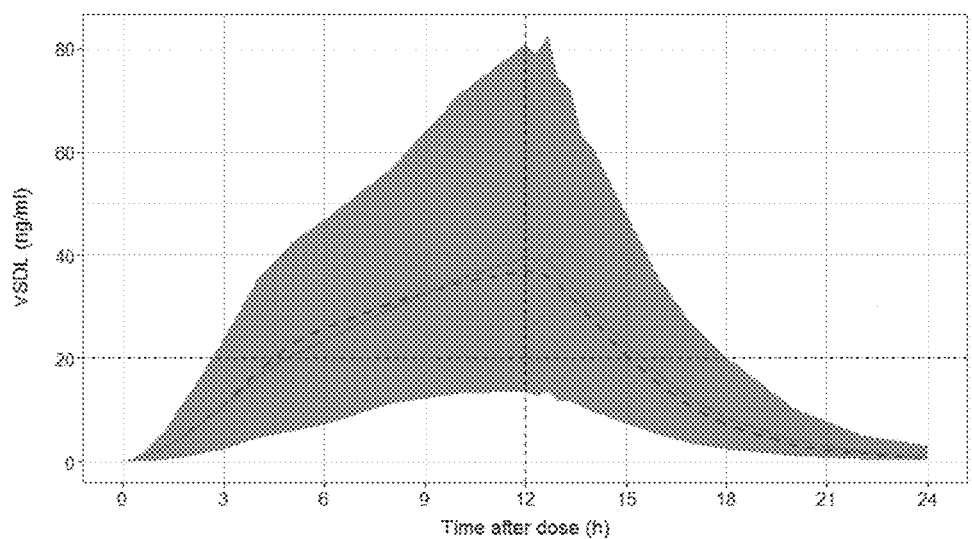
FIG. 19 shows a simulation plot of time (h) after sc dose vs blood plasma VSDL concentration (ng/ml) (1800 μg/h for 5 hours, then 540 μg/h for 7 hours). The dashed line shows population prediction. The black line and ribbon is the mean and 90% CI predicted for 1000 patients.

The predicted VSDL plasma concentrations are shown in FIG. 19. As can be seen, the predicted plasma concentrations in patients infused to target a concentration of 20 ng/ml had a 90% prediction interval of between 8 and 40 ng/ml. The proportional spread of values would be similar regardless of the target concentration.

Example 5—Dosing Subjects to Achieve a Target Css of 5 ng/mL

Method

A dose regimen was designed using the pharmacokinetic model discussed in Example 1. The model was used to simulate the median and 90% prediction intervals for 1000 patients given VSDL at 450 μg/h for 5 h then 135 μg/h for 7 h.

This dose regimen targeted a population value of 5 ng/ml for the period 6-12 h after the start of the infusion.

Figure 20:
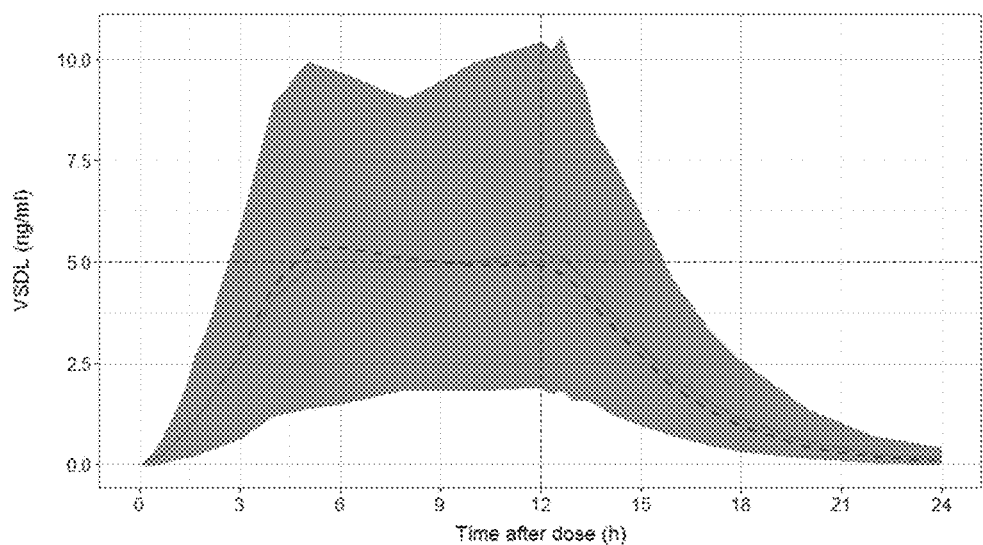
FIG. 20 shows a simulation plot of time (h) after sc dose vs blood plasma VSDL concentration (ng/ml) (450 μg/h for 5 hours, then 135 μg/h for 7 hours). The dashed line shows population prediction. The black line and ribbon is the mean and 90% CI predicted for 1000 patients.

The predicted VSDL plasma concentrations are shown in FIG. 20. The predicted plasma concentrations in patients infused to target a concentration of 5 ng/ml had a 90% prediction interval of between about 2 and 10 ng/ml.

Example 6—Monitoring Plasma VSDL Levels

Monoclonal antibodies (Mabs) to VSDL can be produced using techniques known in the art such as, for example, the procedure exemplified in U.S. Pat. No. 4,196,265, incorporated herein by reference.

To produce detection substrates, the antibodie(s) of interest can be bound to a solid support such as for example glass, polycarbonate, polytetrafluoroethylene, polystyrene, silicon oxide, metal or silicon nitride. This immobilization can either be direct (e.g. by covalent linkage, such as, for example, Schiff's base formation, disulfide linkage, or amide or urea bond formation) or indirect. Methods of generating protein chips are known in the art and are described in for example U.S. Patent Application No. 20020136821, 20020192654, 20020102617 and U.S. Pat. No. 6,391,625.

Specifically, a NUNC plate can be coated with a serial dilution of the selected anti-VSDL capture antibody and incubated overnight at 4° C. After blocking, the plate can be incubated with various dilutions of the test peptide followed by HRP-conjugated secondary detection antibody. The plate can be washed between each addition. The immune reaction can be stopped by the addition of $H_2SO_4$ after an appropriate time based on visual examination of colour, and the OD read in a microplate reader at wavelengths of 450 nm and 620 nm.

The resulting data can be recorded for data analysis. A standard curve can be plotted using an X-Y graph with the mean OD+SD ($OD=OD_{450\ nm}-OD_{620\ nm}$) on the Y axis and the peptide concentration (eg, ng/mL) on the X axis (logarithmic scale).

Example 7—Monitoring Renal Function

Blood or urine samples can be collected at set time points from subjects undergoing treatment according to Examples 2 or Example 3. The creatinine levels in the blood or urine at each time point can be determined using methods described in Israni et al. (2011).

The dosage rate of the VSDL may be increased if the rate of decrease in creatinine levels in the blood or urine over time is not as high as required.

REFERENCES

Israni A K, and Kasiske B L. "Laboratory assessment of kidney disease: glomerular filtration rate, urinalysis, and proteinuria" In: Taal M W, Chertow G M, Marsden P A, et al., eds. *Brenner and Rector's The Kidney.* 9th ed. Philadelphia, Pa.: Elsevier Saunders; 2011: chap 25.

Skelton W P 4th et al., *Anticancer Res* (2) 395-402 (2011).

Vesely D L, Douglass M A, Dietz J R, Gower W R, Jr., McCormick M T, Rodriguez-Paz G, Schocken D D. *Circulation.* 90:1129-1140 (1994).

Vesely D L, Dietz J R, Parks J R, Baig M, McCormick M T, Cintron G, Schocken D D. *Circulation.* 98:323-329 (1998).

Vesely D L, *Am J Physiology* 285:F167-F177 (2003).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of treating a cardio-renal syndrome in a subject, said method comprising administering subcutaneously to the subject an effective amount of an active agent comprising vessel dilator (VSDL) in a multimodal dosage regime comprising at least an initial dosage stage, wherein the initial dose period is from about 4 hours to about 6 hours, and at least one maintenance dosage stage, the initial dosage stage comprising infusing the active agent at an initial dosage rate for an initial period to achieve a target steady state blood plasma concentration of the active agent or metabolite thereof, and the maintenance dosage stage(s) comprising adjusting the dosage rate to a maintenance dosage rate for a maintenance period to substantially maintain said target steady state blood plasma concentration of the active agent or metabolite thereof.

2. The method according to claim 1, wherein the initial dosage rate is from about 20 μg/hour to about 2000 μg/hour.

3. The method according to claim 2, wherein the initial dosage rate is from about 45 μg/hour to about 450 μg/hour.

4. The method according to claim 1, wherein the maintenance dosage rate is from about 20 μg/hour to about 1200 μg/hour.

5. The method according to claim 4, wherein the maintenance dosage rate is from about 20 μg/hour to about 270 μg/hour.

6. The method according to claim 1, wherein the target steady state blood plasma concentration is from about 1 ng/ml to about 15 ng/ml.

7. The method according to claim 1, wherein the target steady state blood plasma concentration is about 5 ng/ml.

8. The method according to claim 1, wherein the initial dosage rate is about 1800 μg/hour.

9. The method according to claim 8, wherein the maintenance dosage rate is about 1080 μg/hour.

10. The method according to claim 8, wherein the maintenance dosage rate is about 540 μg/hour.

11. The method according to claim 1, wherein the initial dosage rate is about 450 μg/hour.

12. The method according to claim 11, wherein the maintenance dosage rate is about 135 μg/hour.

13. The method according to claim 1, wherein the initial dosage rate is about 90 μg/hour.

14. The method according to claim 13, wherein the maintenance dosage rate is about 27 μg/hour.

15. The method according to claim 1, wherein the initial period is about 5 hours.

16. The method according to claim 1, wherein the maintenance period is from about 6 hours to about 8 hours.

17. The method according to claim 16, wherein the maintenance period is about 7 hours.

* * * * *